(12) United States Patent
Barooni

(10) Patent No.: US 11,413,174 B2
(45) Date of Patent: Aug. 16, 2022

(54) CORE ASSEMBLY FOR MEDICAL DEVICE DELIVERY SYSTEMS

(71) Applicant: Covidien LP, Mansfield, MA (US)

(72) Inventor: Agee Barooni, Irvine, CA (US)

(73) Assignee: COVIDIEN LP, Mansfield, MA (US)

( * ) Notice: Subject to any disclaimer, the term of this patent is extended or adjusted under 35 U.S.C. 154(b) by 304 days.

(21) Appl. No.: 16/453,198

(22) Filed: Jun. 26, 2019

(65) Prior Publication Data

US 2020/0405517 A1    Dec. 31, 2020

(51) Int. Cl.
*A61F 2/95* (2013.01)
*A61F 2/962* (2013.01)

(52) U.S. Cl.
CPC ............. *A61F 2/95* (2013.01); *A61F 2/962* (2013.01); *A61F 2002/9511* (2013.01)

(58) Field of Classification Search
CPC ......... A61B 50/00; A61B 50/20; A61B 50/30; A61F 2/24; A61F 2/2418; A61F 2/95; A61F 2002/9505; A61F 2002/9511
See application file for complete search history.

(56) References Cited

U.S. PATENT DOCUMENTS

| | | |
|---|---|---|
| 3,416,531 A | 12/1968 | Lowell |
| 4,364,391 A | 12/1982 | Toye |
| 4,425,919 A | 1/1984 | Alston, Jr. et al. |
| 4,516,972 A | 5/1985 | Samson |
| 4,723,936 A | 2/1988 | Buchbinder et al. |
| 4,877,031 A | 10/1989 | Conway et al. |
| 4,990,151 A | 2/1991 | Wallsten |
| 5,011,478 A | 4/1991 | Cope |
| 5,026,377 A | 6/1991 | Burton et al. |
| 5,037,404 A | 8/1991 | Gold et al. |
| 5,061,275 A | 10/1991 | Wallsten et al. |
| 5,098,393 A | 3/1992 | Amplatz et al. |
| 5,108,411 A | 4/1992 | Mckenzie |
| 5,147,370 A | 9/1992 | Mcnamara et al. |
| 5,178,158 A | 1/1993 | de Toledo |
| 5,201,316 A | 4/1993 | Pomeranz et al. |
| 5,209,734 A | 5/1993 | Hurley et al. |

(Continued)

FOREIGN PATENT DOCUMENTS

| | | |
|---|---|---|
| CN | 104582643 A | 4/2015 |
| CN | 105232195 A | 1/2016 |

(Continued)

OTHER PUBLICATIONS

International Search Report and Written Opinion dated Oct. 15, 2020, International Application No. PCT/US20/70151, 110 pages.

(Continued)

*Primary Examiner* — Christopher D. Prone
(74) *Attorney, Agent, or Firm* — Fortem IP, LLP; Katrina Marcelo; Matthew Lincicum

(57) ABSTRACT

A stent delivery system can include a core assembly sized for insertion into a corporeal lumen and configured for advancing a stent toward a treatment location in the corporeal lumen. The core assembly can include a proximal restraint having a bumper section, a distal section distal to the bumper section, a lumen extending through the bumper and distal sections, and an undercut section including a recess at least partially surrounding the lumen. The recess can abut and/or be formed in the bumper and/or distal sections.

15 Claims, 6 Drawing Sheets

(56) References Cited

U.S. PATENT DOCUMENTS

| | | |
|---|---|---|
| 5,279,562 A | 1/1994 | Sirhan et al. |
| 5,279,596 A | 1/1994 | Castaneda et al. |
| 5,292,311 A | 3/1994 | Cope |
| 5,318,032 A | 6/1994 | Lonsbury et al. |
| 5,318,525 A | 6/1994 | West et al. |
| 5,318,529 A | 6/1994 | Kontos |
| 5,358,493 A | 10/1994 | Schweich, Jr. et al. |
| 5,382,259 A | 1/1995 | Phelps et al. |
| 5,389,087 A | 2/1995 | Miraki |
| 5,403,292 A | 4/1995 | Ju |
| 5,437,288 A | 8/1995 | Schwartz et al. |
| 5,445,646 A | 8/1995 | Euteneuer et al. |
| 5,454,795 A | 10/1995 | Samson |
| 5,458,605 A | 10/1995 | Klemm |
| 5,474,563 A | 12/1995 | Myler et al. |
| 5,478,349 A | 12/1995 | Nicholas |
| 5,484,444 A | 1/1996 | Braunschweiler et al. |
| 5,496,294 A | 3/1996 | Hergenrother et al. |
| 5,499,975 A | 3/1996 | Cope et al. |
| 5,522,822 A | 6/1996 | Phelps et al. |
| 5,531,721 A | 7/1996 | Pepin et al. |
| 5,534,007 A | 7/1996 | St. Germain et al. |
| 5,545,209 A | 8/1996 | Roberts et al. |
| 5,554,139 A | 9/1996 | Okajima |
| 5,569,220 A | 10/1996 | Webster, Jr. |
| 5,571,135 A | 11/1996 | Fraser et al. |
| 5,573,520 A | 11/1996 | Schwartz et al. |
| 5,584,821 A | 12/1996 | Hobbs et al. |
| 5,599,325 A | 2/1997 | Ju et al. |
| 5,599,326 A | 2/1997 | Carter |
| 5,601,539 A | 2/1997 | Corso, Jr. |
| 5,636,641 A | 6/1997 | Fariabi |
| 5,645,559 A | 7/1997 | Hachtman et al. |
| 5,658,264 A | 8/1997 | Samson |
| 5,662,622 A | 9/1997 | Gore et al. |
| 5,676,659 A | 10/1997 | Mcgurk |
| 5,690,644 A * | 11/1997 | Yurek .................. A61F 2/958 623/1.11 |
| 5,695,483 A | 12/1997 | Samson |
| 5,695,499 A | 12/1997 | Helgerson et al. |
| 5,702,373 A | 12/1997 | Samson |
| 5,702,418 A | 12/1997 | Ravenscroft |
| 5,704,926 A | 1/1998 | Sutton |
| 5,709,703 A | 1/1998 | Lukic et al. |
| 5,711,909 A | 1/1998 | Gore et al. |
| 5,725,513 A | 3/1998 | Ju et al. |
| 5,725,571 A | 3/1998 | Imbert et al. |
| 5,728,063 A | 3/1998 | Preissman et al. |
| 5,741,429 A | 4/1998 | Donadio, III et al. |
| 5,743,876 A | 4/1998 | Swanson |
| 5,755,777 A | 5/1998 | Chuter |
| 5,759,173 A | 6/1998 | Preissman et al. |
| 5,776,141 A | 7/1998 | Klein et al. |
| 5,782,811 A | 7/1998 | Samson et al. |
| 5,791,036 A | 8/1998 | Goodin et al. |
| 5,824,041 A | 10/1998 | Lenker et al. |
| 5,833,632 A | 11/1998 | Jacobsen et al. |
| 5,836,925 A | 11/1998 | Soltesz |
| 5,836,926 A | 11/1998 | Peterson et al. |
| 5,851,203 A | 12/1998 | Van Muiden |
| 5,853,400 A | 12/1998 | Samson |
| 5,873,866 A | 2/1999 | Kondo et al. |
| 5,891,112 A | 4/1999 | Samson |
| 5,897,529 A | 4/1999 | Ponzi |
| 5,897,537 A | 4/1999 | Berg et al. |
| 5,902,290 A | 5/1999 | Peacock, III et al. |
| 5,906,605 A | 5/1999 | Coxum |
| 5,935,161 A | 8/1999 | Robinson et al. |
| 5,938,653 A | 8/1999 | Pepin |
| 5,951,494 A | 9/1999 | Wang et al. |
| 5,951,539 A | 9/1999 | Nita et al. |
| 5,961,510 A | 10/1999 | Fugoso et al. |
| 5,968,053 A | 10/1999 | Revelas |
| 5,968,069 A | 10/1999 | Dusbabek et al. |
| 5,971,975 A | 10/1999 | Mills et al. |
| 5,984,963 A | 11/1999 | Ryan et al. |
| 6,017,323 A | 1/2000 | Chee |
| 6,030,371 A | 2/2000 | Pursley |
| 6,045,547 A | 4/2000 | Ren et al. |
| 6,053,903 A | 4/2000 | Samson |
| 6,053,904 A | 4/2000 | Scribner et al. |
| 6,077,258 A | 6/2000 | Lange et al. |
| 6,077,295 A | 6/2000 | Limon et al. |
| 6,077,297 A | 6/2000 | Robinson et al. |
| 6,083,152 A | 7/2000 | Strong |
| 6,093,177 A | 7/2000 | Javier, Jr. et al. |
| 6,105,651 A | 8/2000 | Leanna |
| 6,106,510 A | 8/2000 | Lunn et al. |
| 6,106,540 A | 8/2000 | Dehdashtian et al. |
| 6,123,723 A | 9/2000 | Konya et al. |
| 6,126,685 A | 10/2000 | Lenker et al. |
| 6,135,992 A | 10/2000 | Wang |
| 6,149,680 A | 11/2000 | Shelso et al. |
| 6,152,912 A | 11/2000 | Jansen et al. |
| 6,152,944 A | 11/2000 | Holman et al. |
| 6,159,219 A | 12/2000 | Ren |
| 6,165,163 A | 12/2000 | Chien et al. |
| 6,165,166 A | 12/2000 | Samuelson et al. |
| 6,171,295 B1 | 1/2001 | Garabedian et al. |
| 6,171,296 B1 | 1/2001 | Chow |
| 6,171,297 B1 | 1/2001 | Pedersen et al. |
| 6,186,986 B1 | 2/2001 | Berg et al. |
| 6,193,739 B1 | 2/2001 | Chevillon et al. |
| 6,197,015 B1 | 3/2001 | Wilson |
| 6,217,565 B1 | 4/2001 | Cohen |
| 6,217,566 B1 | 4/2001 | Ju et al. |
| 6,251,132 B1 | 6/2001 | Ravenscroft et al. |
| 6,258,080 B1 | 7/2001 | Samson |
| 6,264,683 B1 | 7/2001 | Stack et al. |
| 6,287,315 B1 | 9/2001 | Wijeratne et al. |
| 6,325,807 B1 | 12/2001 | Que |
| 6,350,278 B1 | 2/2002 | Lenker et al. |
| 6,355,027 B1 | 3/2002 | Le et al. |
| 6,358,238 B1 | 3/2002 | Sherry |
| 6,358,460 B1 | 3/2002 | Hunt, Jr. et al. |
| 6,368,316 B1 | 4/2002 | Jansen et al. |
| 6,371,953 B1 | 4/2002 | Beyar et al. |
| 6,383,171 B1 | 5/2002 | Gifford et al. |
| 6,387,118 B1 | 5/2002 | Hanson |
| 6,389,087 B1 | 5/2002 | Heinonen et al. |
| 6,395,008 B1 | 5/2002 | Ellis et al. |
| 6,395,017 B1 | 5/2002 | Dwyer et al. |
| 6,398,791 B1 | 6/2002 | Que et al. |
| 6,419,693 B1 | 7/2002 | Fariabi |
| 6,425,898 B1 | 7/2002 | Wilson et al. |
| 6,428,552 B1 | 8/2002 | Sparks |
| 6,443,971 B1 | 9/2002 | Boylan et al. |
| 6,458,075 B1 | 10/2002 | Sugiyama et al. |
| 6,464,684 B1 | 10/2002 | Galdonik |
| 6,468,298 B1 | 10/2002 | Pelton |
| 6,475,184 B1 | 11/2002 | Wang et al. |
| 6,494,907 B1 | 12/2002 | Bulver |
| 6,508,804 B2 | 1/2003 | Sarge et al. |
| 6,508,805 B1 | 1/2003 | Garabedian et al. |
| 6,508,806 B1 | 1/2003 | Hoste |
| 6,517,547 B1 | 2/2003 | Feeser et al. |
| 6,554,820 B1 | 4/2003 | Wendlandt et al. |
| 6,562,021 B1 | 5/2003 | Derbin et al. |
| 6,562,063 B1 | 5/2003 | Euteneuer et al. |
| 6,576,006 B2 | 6/2003 | Limon et al. |
| 6,582,460 B1 | 6/2003 | Cryer |
| 6,589,227 B2 | 7/2003 | Soenderskov Klint |
| 6,602,271 B2 | 8/2003 | Adams et al. |
| 6,607,551 B1 | 8/2003 | Sullivan et al. |
| 6,622,367 B1 | 9/2003 | Bolduc et al. |
| 6,635,047 B2 | 10/2003 | Forsberg |
| 6,638,245 B2 | 10/2003 | Miller et al. |
| 6,641,564 B1 | 11/2003 | Kraus |
| 6,648,654 B1 | 11/2003 | Hembree |
| 6,648,874 B2 | 11/2003 | Parisi et al. |
| 6,652,508 B2 | 11/2003 | Griffin et al. |
| 6,663,614 B1 | 12/2003 | Carter |
| 6,669,719 B2 | 12/2003 | Wallace et al. |
| 6,689,120 B1 | 2/2004 | Gerdts |

(56) References Cited

U.S. PATENT DOCUMENTS

| | | |
|---|---|---|
| 6,699,274 B2 | 3/2004 | Stinson |
| 6,702,782 B2 | 3/2004 | Miller et al. |
| 6,706,055 B2 | 3/2004 | Douk et al. |
| 6,716,207 B2 | 4/2004 | Farnholtz |
| 6,726,659 B1 | 4/2004 | Stocking et al. |
| 6,764,504 B2 | 7/2004 | Wang et al. |
| 6,808,529 B2 | 10/2004 | Fulkerson |
| 6,814,749 B2 | 11/2004 | Cox et al. |
| 6,815,325 B2 | 11/2004 | Ishii |
| 6,817,995 B1 | 11/2004 | Halpern |
| 6,830,575 B2 | 12/2004 | Stenzel et al. |
| 6,837,890 B1 | 1/2005 | Chludzinski et al. |
| 6,843,802 B1 | 1/2005 | Villalobos et al. |
| 6,858,024 B1 | 2/2005 | Berg et al. |
| 6,858,034 B1 * | 2/2005 | Hijlkema ............... A61F 2/95 606/108 |
| 6,866,660 B2 | 3/2005 | Garabedian et al. |
| 6,866,679 B2 | 3/2005 | Kusleika |
| 6,932,837 B2 | 8/2005 | Amplatz et al. |
| 6,939,353 B2 | 9/2005 | Que et al. |
| 6,945,970 B2 | 9/2005 | Pepin |
| 6,960,227 B2 | 11/2005 | Jones et al. |
| 6,984,963 B2 | 1/2006 | Pidutti et al. |
| 6,989,024 B2 | 1/2006 | Hebert et al. |
| 7,001,369 B2 | 2/2006 | Griffin et al. |
| 7,011,675 B2 | 3/2006 | Hemerick et al. |
| 7,025,758 B2 | 4/2006 | Klint |
| 7,074,236 B2 | 7/2006 | Rabkin et al. |
| 7,104,979 B2 | 9/2006 | Jansen et al. |
| 7,147,656 B2 | 12/2006 | Andreas et al. |
| 7,156,860 B2 | 1/2007 | Wallsten |
| 7,163,523 B2 | 1/2007 | Devens, Jr. et al. |
| 7,166,088 B2 | 1/2007 | Heuser |
| 7,166,099 B2 | 1/2007 | Devens, Jr. |
| 7,166,100 B2 | 1/2007 | Jordan et al. |
| 7,172,575 B2 | 2/2007 | El-Nounou et al. |
| 7,223,263 B1 | 5/2007 | Seno |
| 7,228,878 B2 | 6/2007 | Chen et al. |
| 7,306,624 B2 | 12/2007 | Yodfat et al. |
| 7,323,000 B2 | 1/2008 | Monstdt et al. |
| 7,331,948 B2 | 2/2008 | Skarda |
| 7,357,812 B2 | 4/2008 | Andreas et al. |
| 7,371,248 B2 | 5/2008 | Dapolito et al. |
| 7,402,151 B2 | 7/2008 | Rosenman et al. |
| 7,404,820 B2 | 7/2008 | Mazzocchi et al. |
| 7,427,288 B2 | 9/2008 | Sater |
| 7,438,712 B2 | 10/2008 | Chouinard |
| 7,445,684 B2 | 11/2008 | Pursley |
| 7,473,271 B2 | 1/2009 | Gunderson |
| 7,473,272 B2 | 1/2009 | Pryor |
| 7,481,804 B2 | 1/2009 | Devens, Jr. |
| 7,507,229 B2 | 3/2009 | Hewitt et al. |
| 7,524,322 B2 | 4/2009 | Monstdt et al. |
| 7,556,634 B2 | 7/2009 | Lee et al. |
| 7,556,710 B2 | 7/2009 | Leeflang et al. |
| 7,569,046 B2 | 8/2009 | Zhou |
| 7,572,290 B2 | 8/2009 | Yodfat et al. |
| 7,582,079 B2 | 9/2009 | Wendlandt et al. |
| 7,597,830 B2 | 10/2009 | Zhou |
| 7,621,904 B2 | 11/2009 | Mcferran et al. |
| 7,641,646 B2 | 1/2010 | Kennedy, II |
| 7,651,520 B2 | 1/2010 | Fischell et al. |
| 7,655,031 B2 | 2/2010 | Tenne et al. |
| 7,674,411 B2 | 3/2010 | Berg et al. |
| 7,691,138 B2 | 4/2010 | Stenzel et al. |
| 7,708,704 B2 | 5/2010 | Mitelberg et al. |
| 7,717,953 B2 | 5/2010 | Kaplan et al. |
| 7,740,652 B2 | 6/2010 | Gerdts et al. |
| 7,758,624 B2 | 7/2010 | Dorn et al. |
| 7,766,820 B2 | 8/2010 | Core |
| 7,766,896 B2 | 8/2010 | Kornkven Volk et al. |
| 7,780,646 B2 | 8/2010 | Farnholtz |
| 7,815,600 B2 | 10/2010 | Al-Marashi et al. |
| 7,815,608 B2 | 10/2010 | Schafersman et al. |
| 7,815,628 B2 | 10/2010 | Devens, Jr. |
| 7,828,790 B2 | 11/2010 | Griffin |
| 7,867,267 B2 | 1/2011 | Sullivan et al. |
| 7,879,022 B2 | 2/2011 | Bonnette et al. |
| 7,935,140 B2 | 5/2011 | Griffin |
| 7,942,925 B2 | 5/2011 | Yodfat et al. |
| 7,955,370 B2 | 6/2011 | Gunderson |
| 7,981,148 B2 | 7/2011 | Aguilar et al. |
| 7,993,385 B2 | 8/2011 | Levine et al. |
| 8,025,692 B2 | 9/2011 | Feeser |
| 8,034,095 B2 | 10/2011 | Randolph et al. |
| 8,042,720 B2 | 10/2011 | Shifrin et al. |
| 8,048,104 B2 | 11/2011 | Monstadt et al. |
| 8,066,754 B2 | 11/2011 | Malewicz |
| 8,083,791 B2 | 12/2011 | Kaplan et al. |
| 8,088,140 B2 | 1/2012 | Ferrera et al. |
| 8,092,508 B2 | 1/2012 | Leynov et al. |
| 8,109,987 B2 | 2/2012 | Kaplan et al. |
| 8,133,266 B2 | 3/2012 | Thomas et al. |
| 8,147,534 B2 | 4/2012 | Berez et al. |
| 8,187,314 B2 | 5/2012 | Davis et al. |
| 8,257,432 B2 | 9/2012 | Kaplan et al. |
| 8,298,276 B2 | 10/2012 | Ozawa et al. |
| 8,317,850 B2 | 11/2012 | Kusleika |
| 8,337,543 B2 | 12/2012 | Jordan et al. |
| 8,366,763 B2 | 2/2013 | Davis et al. |
| 8,382,818 B2 | 2/2013 | Davis et al. |
| 8,480,701 B2 | 7/2013 | Monstadt |
| 8,579,958 B2 | 11/2013 | Kusleika |
| 8,591,566 B2 | 11/2013 | Newell et al. |
| 8,597,321 B2 | 12/2013 | Monstadt et al. |
| 8,636,760 B2 | 1/2014 | Garcia et al. |
| 8,679,172 B2 | 3/2014 | Dorn et al. |
| 8,790,387 B2 | 7/2014 | Nguyen et al. |
| 8,858,613 B2 | 10/2014 | Cragg et al. |
| 8,968,383 B1 | 3/2015 | Johnson et al. |
| 9,393,141 B2 | 7/2016 | Gerdts et al. |
| 9,439,795 B2 | 9/2016 | Wang et al. |
| 9,474,639 B2 | 10/2016 | Haggstrom et al. |
| 9,775,733 B2 | 10/2017 | Johnson et al. |
| 9,782,186 B2 | 10/2017 | Johnson et al. |
| 9,827,126 B2 | 11/2017 | Losordo et al. |
| 10,786,377 B2 | 9/2020 | Nageswaran et al. |
| 11,071,637 B2 | 7/2021 | Dawson et al. |
| 2001/0020173 A1 | 9/2001 | Klumb et al. |
| 2001/0027310 A1 | 10/2001 | Parisi et al. |
| 2001/0029362 A1 | 10/2001 | Sirhan et al. |
| 2001/0044591 A1 | 11/2001 | Stevens et al. |
| 2001/0049547 A1 | 12/2001 | Moore |
| 2002/0029046 A1 | 3/2002 | Lorentzen et al. |
| 2002/0045929 A1 | 4/2002 | Diaz |
| 2002/0049412 A1 | 4/2002 | Madrid et al. |
| 2002/0072789 A1 | 6/2002 | Hackett et al. |
| 2002/0107526 A1 | 8/2002 | Greenberg et al. |
| 2002/0111666 A1 | 8/2002 | Hart et al. |
| 2002/0138128 A1 | 9/2002 | Stiger et al. |
| 2002/0156459 A1 | 10/2002 | Ye et al. |
| 2002/0156460 A1 | 10/2002 | Ye et al. |
| 2002/0165523 A1 | 11/2002 | Chin et al. |
| 2002/0188342 A1 | 12/2002 | Rykhus et al. |
| 2003/0004539 A1 | 1/2003 | Linder et al. |
| 2003/0009208 A1 | 1/2003 | Snyder et al. |
| 2003/0050600 A1 | 3/2003 | Ressemann et al. |
| 2003/0181827 A1 | 9/2003 | Hojeibane et al. |
| 2003/0191451 A1 | 10/2003 | Gilmartin |
| 2003/0212410 A1 | 11/2003 | Stenzel et al. |
| 2003/0212430 A1 | 11/2003 | Bose et al. |
| 2004/0024416 A1 | 2/2004 | Yodfat et al. |
| 2004/0092868 A1 | 5/2004 | Murray |
| 2004/0092879 A1 | 5/2004 | Kraus et al. |
| 2004/0111095 A1 | 6/2004 | Gordon et al. |
| 2004/0143239 A1 | 7/2004 | Zhou et al. |
| 2004/0147903 A1 | 7/2004 | Latini |
| 2004/0158230 A1 | 8/2004 | Hunn et al. |
| 2004/0181174 A2 | 9/2004 | Davis et al. |
| 2004/0193140 A1 | 9/2004 | Griffin et al. |
| 2004/0193243 A1 | 9/2004 | Mangiardi et al. |
| 2004/0204749 A1 | 10/2004 | Gunderson |
| 2004/0220585 A1 | 11/2004 | Nikolchev et al. |
| 2004/0230285 A1 | 11/2004 | Gifford et al. |

(56) References Cited

U.S. PATENT DOCUMENTS

| | | |
|---|---|---|
| 2004/0260271 A1 | 12/2004 | Huyser et al. |
| 2004/0260384 A1 | 12/2004 | Allen |
| 2004/0267348 A1 | 12/2004 | Gunderson et al. |
| 2005/0033403 A1 | 2/2005 | Ward et al. |
| 2005/0070794 A1 | 3/2005 | Deal et al. |
| 2005/0090802 A1 | 4/2005 | Connors et al. |
| 2005/0096724 A1 | 5/2005 | Stenzel et al. |
| 2005/0119719 A1 | 6/2005 | Wallace et al. |
| 2005/0125051 A1 | 6/2005 | Eidenschink et al. |
| 2005/0131449 A1 | 6/2005 | Salahieh et al. |
| 2005/0143773 A1 | 6/2005 | Abrams et al. |
| 2005/0149160 A1 | 7/2005 | Mcferran |
| 2005/0182388 A1 | 8/2005 | Garabedian et al. |
| 2005/0182475 A1 | 8/2005 | Jen et al. |
| 2005/0228361 A1 | 10/2005 | Tremaglio |
| 2005/0240254 A1 | 10/2005 | Austin |
| 2005/0273149 A1 | 12/2005 | Tran et al. |
| 2005/0277949 A1 | 12/2005 | Que et al. |
| 2006/0030835 A1 | 2/2006 | Sherman et al. |
| 2006/0036309 A1 | 2/2006 | Hebert et al. |
| 2006/0058865 A1 | 3/2006 | Case et al. |
| 2006/0064123 A1 | 3/2006 | Bonnette et al. |
| 2006/0074477 A1 | 4/2006 | Berthiaume et al. |
| 2006/0089618 A1 | 4/2006 | Mcferran et al. |
| 2006/0095050 A1 | 5/2006 | Hartley et al. |
| 2006/0100687 A1 | 5/2006 | Fahey et al. |
| 2006/0100688 A1 | 5/2006 | Jordan et al. |
| 2006/0116750 A1 | 6/2006 | Hebert et al. |
| 2006/0129166 A1 | 6/2006 | Lavelle |
| 2006/0178698 A1 | 8/2006 | Mcintyre et al. |
| 2006/0184226 A1 | 8/2006 | Austin |
| 2006/0212042 A1 | 9/2006 | Lamport et al. |
| 2006/0217682 A1 | 9/2006 | Stivland et al. |
| 2006/0235502 A1 | 10/2006 | Belluche et al. |
| 2007/0027520 A1 | 2/2007 | Sherburne |
| 2007/0043430 A1 | 2/2007 | Stinson |
| 2007/0049903 A1 | 3/2007 | Jansen et al. |
| 2007/0078504 A1 | 4/2007 | Mialhe |
| 2007/0088323 A1 | 4/2007 | Campbell et al. |
| 2007/0100421 A1 | 5/2007 | Griffin |
| 2007/0117645 A1 | 5/2007 | Nakashima |
| 2007/0129706 A1 | 6/2007 | Katoh et al. |
| 2007/0149927 A1 | 6/2007 | Itou et al. |
| 2007/0161956 A1 | 7/2007 | Heuser |
| 2007/0185446 A1 | 8/2007 | Accisano |
| 2007/0203563 A1 | 8/2007 | Hebert et al. |
| 2007/0233224 A1 | 10/2007 | Leynov et al. |
| 2007/0239254 A1 | 10/2007 | Chia et al. |
| 2007/0239261 A1 | 10/2007 | Bose et al. |
| 2007/0250039 A1 | 10/2007 | Lobbins et al. |
| 2007/0250040 A1 | 10/2007 | Provost et al. |
| 2007/0255255 A1 | 11/2007 | Shah et al. |
| 2007/0255388 A1 | 11/2007 | Rudakov et al. |
| 2007/0270779 A1 | 11/2007 | Jacobs et al. |
| 2007/0299424 A1 | 12/2007 | Cumming et al. |
| 2007/0299500 A1 | 12/2007 | Hebert et al. |
| 2007/0299501 A1 | 12/2007 | Hebert et al. |
| 2007/0299502 A1 | 12/2007 | Hebert et al. |
| 2008/0009934 A1 | 1/2008 | Schneider et al. |
| 2008/0015558 A1 | 1/2008 | Harlan |
| 2008/0015678 A1 | 1/2008 | Kaplan et al. |
| 2008/0027528 A1 | 1/2008 | Jagger et al. |
| 2008/0033399 A1 | 2/2008 | Hunn et al. |
| 2008/0033528 A1 | 2/2008 | Satasiya et al. |
| 2008/0051705 A1 | 2/2008 | Von et al. |
| 2008/0051761 A1 | 2/2008 | Slazas et al. |
| 2008/0071301 A1 | 3/2008 | Matsuura et al. |
| 2008/0077229 A1 | 3/2008 | Andreas et al. |
| 2008/0082083 A1 | 4/2008 | Forde et al. |
| 2008/0091169 A1 | 4/2008 | Heideman et al. |
| 2008/0097398 A1 | 4/2008 | Mitelberg et al. |
| 2008/0108974 A1 | 5/2008 | Yee |
| 2008/0132933 A1 | 6/2008 | Gerber |
| 2008/0140180 A1 | 6/2008 | Dolan et al. |
| 2008/0147001 A1 | 6/2008 | Al-marashi et al. |
| 2008/0147162 A1 | 6/2008 | Andreas et al. |
| 2008/0177249 A1 | 7/2008 | Heuser et al. |
| 2008/0188865 A1 | 8/2008 | Miller et al. |
| 2008/0188928 A1 | 8/2008 | Salahieh et al. |
| 2008/0221666 A1 | 9/2008 | Licata et al. |
| 2008/0234660 A2 | 9/2008 | Cumming et al. |
| 2008/0234795 A1 | 9/2008 | Snow et al. |
| 2008/0243225 A1 | 10/2008 | Satasiya et al. |
| 2008/0255541 A1 | 10/2008 | Hoffman et al. |
| 2008/0255653 A1 | 10/2008 | Schkolnik |
| 2008/0255654 A1 | 10/2008 | Hebert et al. |
| 2008/0262471 A1 | 10/2008 | Warnock |
| 2008/0262472 A1 | 10/2008 | Lunn et al. |
| 2008/0262592 A1 | 10/2008 | Jordan et al. |
| 2008/0275426 A1 | 11/2008 | Holman et al. |
| 2008/0300667 A1 | 12/2008 | Hebert et al. |
| 2008/0312639 A1 | 12/2008 | Weber |
| 2009/0012500 A1 | 1/2009 | Murata et al. |
| 2009/0082609 A1 | 3/2009 | Condado |
| 2009/0105802 A1 | 4/2009 | Henry et al. |
| 2009/0125053 A1 | 5/2009 | Ferrera et al. |
| 2009/0132019 A1 | 5/2009 | Duffy et al. |
| 2009/0138066 A1 | 5/2009 | Leopold et al. |
| 2009/0143849 A1 | 6/2009 | Ozawa et al. |
| 2009/0149835 A1 | 6/2009 | Velasco et al. |
| 2009/0157048 A1 | 6/2009 | Sutermeister et al. |
| 2009/0160112 A1 | 6/2009 | Ostrovsky |
| 2009/0171319 A1 | 7/2009 | Guo et al. |
| 2009/0204196 A1 | 8/2009 | Weber |
| 2009/0240235 A1 | 9/2009 | Murata |
| 2009/0264985 A1 | 10/2009 | Bruszewski |
| 2009/0287182 A1 | 11/2009 | Bishop et al. |
| 2009/0287183 A1 | 11/2009 | Bishop et al. |
| 2009/0287187 A1 | 11/2009 | Legaspi et al. |
| 2009/0287292 A1 | 11/2009 | Becking et al. |
| 2009/0299333 A1 | 12/2009 | Wendlandt et al. |
| 2009/0299449 A1 | 12/2009 | Styrc |
| 2009/0318947 A1 | 12/2009 | Garcia et al. |
| 2010/0020354 A1 | 1/2010 | Ito |
| 2010/0036363 A1 | 2/2010 | Watanabe et al. |
| 2010/0049293 A1 | 2/2010 | Zukowski et al. |
| 2010/0049297 A1 | 2/2010 | Dorn |
| 2010/0057184 A1 | 3/2010 | Randolph et al. |
| 2010/0057185 A1 | 3/2010 | Melsheimer et al. |
| 2010/0069852 A1 | 3/2010 | Kelley |
| 2010/0087913 A1 | 4/2010 | Rabkin et al. |
| 2010/0094258 A1 | 4/2010 | Shimogami et al. |
| 2010/0094394 A1 | 4/2010 | Beach et al. |
| 2010/0094395 A1 | 4/2010 | Kellett |
| 2010/0100106 A1 | 4/2010 | Ferrera |
| 2010/0160863 A1 | 6/2010 | Heuser |
| 2010/0198334 A1 | 8/2010 | Yodfat et al. |
| 2010/0204770 A1 | 8/2010 | Mas et al. |
| 2010/0217235 A1 | 8/2010 | Thorstenson et al. |
| 2010/0256602 A1 | 10/2010 | Lippert et al. |
| 2010/0256603 A1 | 10/2010 | Lippert et al. |
| 2010/0262157 A1 | 10/2010 | Silver et al. |
| 2010/0268243 A1 | 10/2010 | Parker |
| 2010/0268328 A1 | 10/2010 | Stiger |
| 2010/0274270 A1 | 10/2010 | Patel et al. |
| 2010/0298931 A1 | 11/2010 | Quadri et al. |
| 2010/0331951 A1 | 12/2010 | Bei et al. |
| 2011/0009943 A1 | 1/2011 | Paul et al. |
| 2011/0022157 A1 | 1/2011 | Essinger et al. |
| 2011/0029065 A1 | 2/2011 | Wood et al. |
| 2011/0034987 A1 | 2/2011 | Kennedy |
| 2011/0054586 A1 | 3/2011 | Mayberry et al. |
| 2011/0093055 A1 | 4/2011 | Kujawski |
| 2011/0098804 A1 | 4/2011 | Yeung et al. |
| 2011/0106235 A1 | 5/2011 | Haverkost et al. |
| 2011/0112623 A1 | 5/2011 | Schatz |
| 2011/0137403 A1 | 6/2011 | Rasmussen et al. |
| 2011/0152760 A1 | 6/2011 | Parker |
| 2011/0160763 A1 | 6/2011 | Ferrera et al. |
| 2011/0178588 A1 | 7/2011 | Haselby |
| 2011/0190862 A1 | 8/2011 | Bashiri et al. |
| 2011/0190865 A1 | 8/2011 | Mchugo et al. |
| 2011/0208292 A1 | 8/2011 | Von et al. |
| 2011/0224650 A1 | 9/2011 | Itou et al. |

(56) References Cited

U.S. PATENT DOCUMENTS

| | | |
|---|---|---|
| 2011/0257720 A1 | 10/2011 | Peterson et al. |
| 2011/0288626 A1 | 11/2011 | Straubinger et al. |
| 2011/0319904 A1 | 12/2011 | Hollett et al. |
| 2012/0029607 A1 | 2/2012 | Mchugo et al. |
| 2012/0035700 A1 | 2/2012 | Leanna et al. |
| 2012/0053681 A1 | 3/2012 | Alkhatib et al. |
| 2012/0059449 A1 | 3/2012 | Dorn et al. |
| 2012/0065660 A1 | 3/2012 | Ferrera et al. |
| 2012/0116494 A1 | 5/2012 | Leynov et al. |
| 2012/0123511 A1 | 5/2012 | Brown |
| 2012/0226343 A1 | 9/2012 | Vo et al. |
| 2012/0253447 A1 | 10/2012 | Hayasaka et al. |
| 2012/0316638 A1 | 12/2012 | Grad et al. |
| 2013/0085562 A1 | 4/2013 | Rincon et al. |
| 2013/0131775 A1 | 5/2013 | Hadley et al. |
| 2013/0172925 A1 | 7/2013 | Garcia et al. |
| 2013/0172979 A1 | 7/2013 | Fargahi |
| 2013/0226276 A1 | 8/2013 | Newell et al. |
| 2013/0226278 A1 | 8/2013 | Newell et al. |
| 2013/0261730 A1 | 10/2013 | Bose et al. |
| 2013/0274618 A1 | 10/2013 | Hou et al. |
| 2013/0274859 A1 | 10/2013 | Argentine |
| 2013/0282099 A1 | 10/2013 | Huynh |
| 2013/0304185 A1 | 11/2013 | Newell et al. |
| 2014/0025150 A1 | 1/2014 | Lim |
| 2014/0031918 A1 | 1/2014 | Newell et al. |
| 2014/0148893 A1 | 5/2014 | Kusleika |
| 2014/0171826 A1 | 6/2014 | Lampropoulos et al. |
| 2014/0172067 A1 | 6/2014 | Brown et al. |
| 2014/0194919 A1 | 7/2014 | Losordo et al. |
| 2014/0200648 A1 | 7/2014 | Newell et al. |
| 2014/0277332 A1 | 9/2014 | Slazas et al. |
| 2014/0324148 A1 | 10/2014 | Nishigishi |
| 2015/0032198 A1 | 1/2015 | Folk |
| 2015/0066128 A1 | 3/2015 | Losordo et al. |
| 2015/0066129 A1 | 3/2015 | Nageswaran et al. |
| 2015/0066130 A1 | 3/2015 | Haggstrom et al. |
| 2015/0066131 A1 | 3/2015 | Luong et al. |
| 2015/0080937 A1 | 3/2015 | Davidson |
| 2015/0133990 A1 | 5/2015 | Davidson |
| 2015/0164666 A1 | 6/2015 | Johnson et al. |
| 2015/0238336 A1 | 8/2015 | Johnson et al. |
| 2016/0113793 A1 | 4/2016 | Nishigishi |
| 2016/0206454 A1 | 7/2016 | Fischell et al. |
| 2017/0035592 A1 | 2/2017 | Haggstrom et al. |
| 2017/0252161 A1 | 9/2017 | Tran et al. |
| 2018/0042745 A1 | 2/2018 | Losordo et al. |
| 2018/0200092 A1 | 7/2018 | Nageswaran et al. |
| 2018/0263764 A1* | 9/2018 | Manash .................... A61F 2/24 |
| 2018/0263799 A1 | 9/2018 | Elwood et al. |
| 2019/0314175 A1 | 10/2019 | Dawson et al. |
| 2019/0314176 A1 | 10/2019 | Nageswaran et al. |
| 2019/0314177 A1 | 10/2019 | Alonso et al. |
| 2019/0314179 A1 | 10/2019 | Nageswaran et al. |
| 2019/0374358 A1 | 12/2019 | Nageswaran |
| 2020/0375769 A1 | 12/2020 | Nageswaran et al. |

FOREIGN PATENT DOCUMENTS

| | | |
|---|---|---|
| EP | 1344502 A2 | 9/2003 |
| WO | 9719713 A2 | 6/1997 |
| WO | WO 9820811 A1 | 5/1998 |
| WO | WO 2010127838 A2 | 11/2010 |
| WO | WO 2011076408 A1 | 6/2011 |
| WO | WO 2011081997 A1 | 7/2011 |
| WO | WO 2012158152 A1 | 11/2012 |
| WO | 2014074462 A2 | 5/2014 |

OTHER PUBLICATIONS

Search Report dated Mar. 24, 2020, CN Application No. 201880007614.9, 10 pages.

* cited by examiner

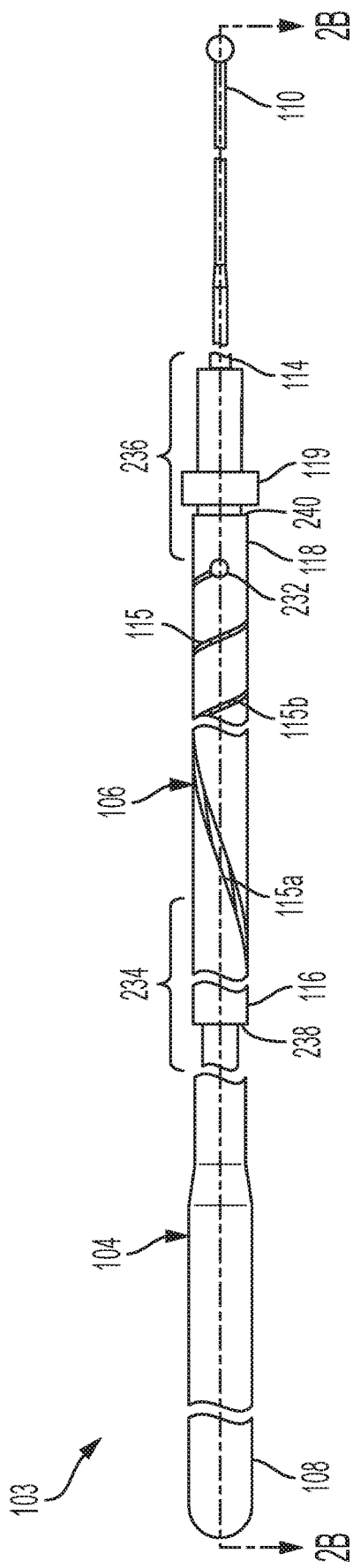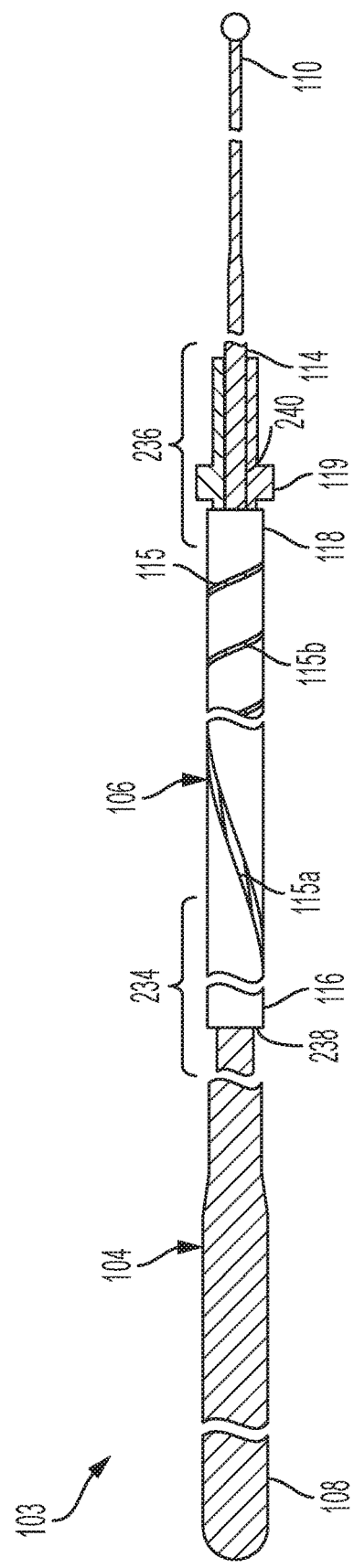
FIG. 2A
FIG. 2B

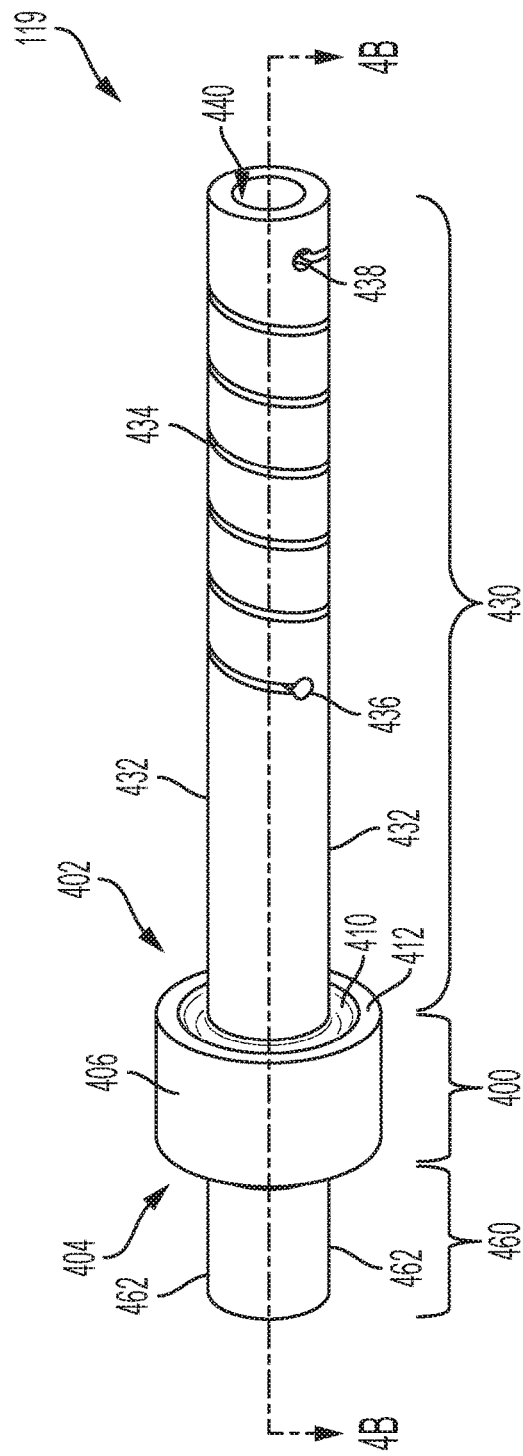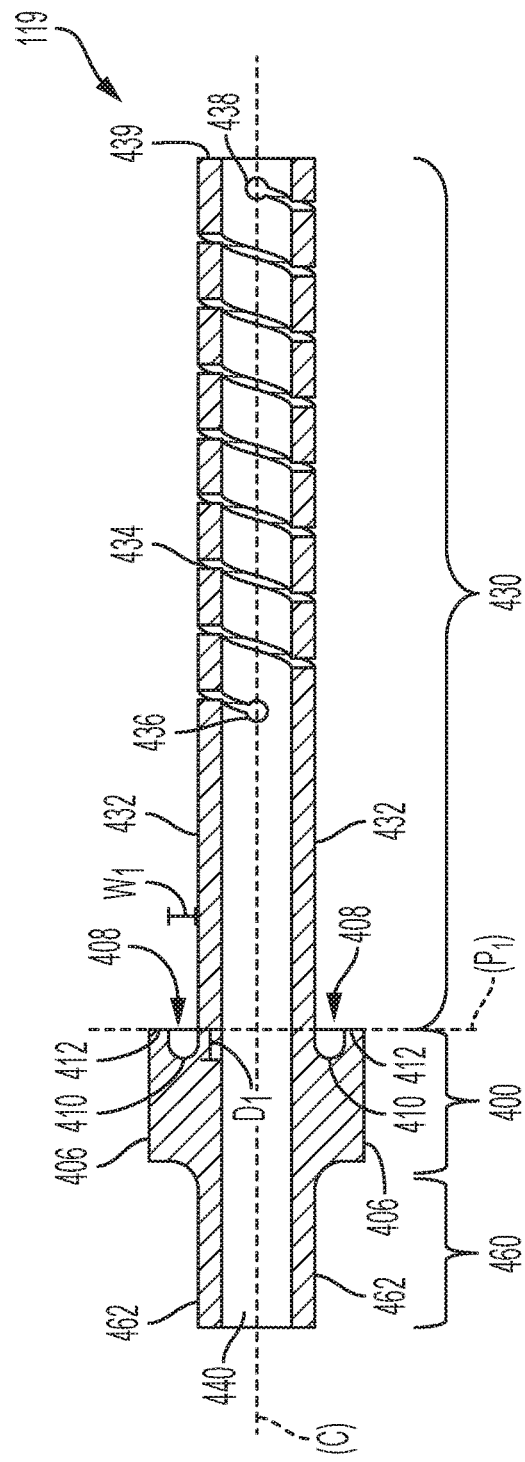

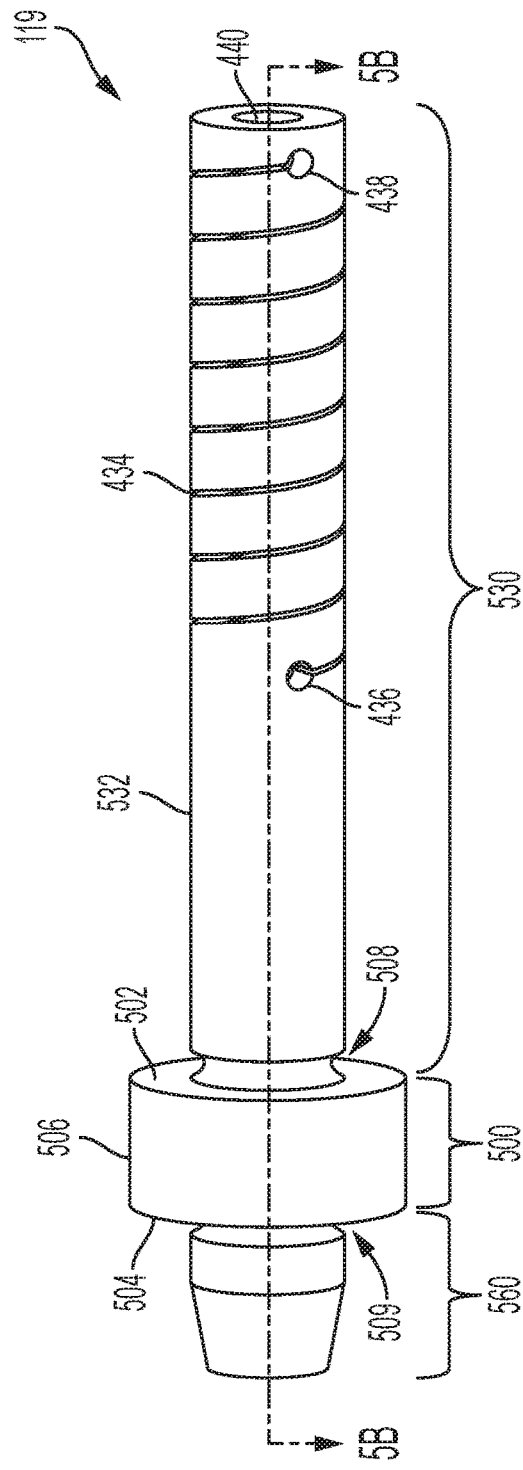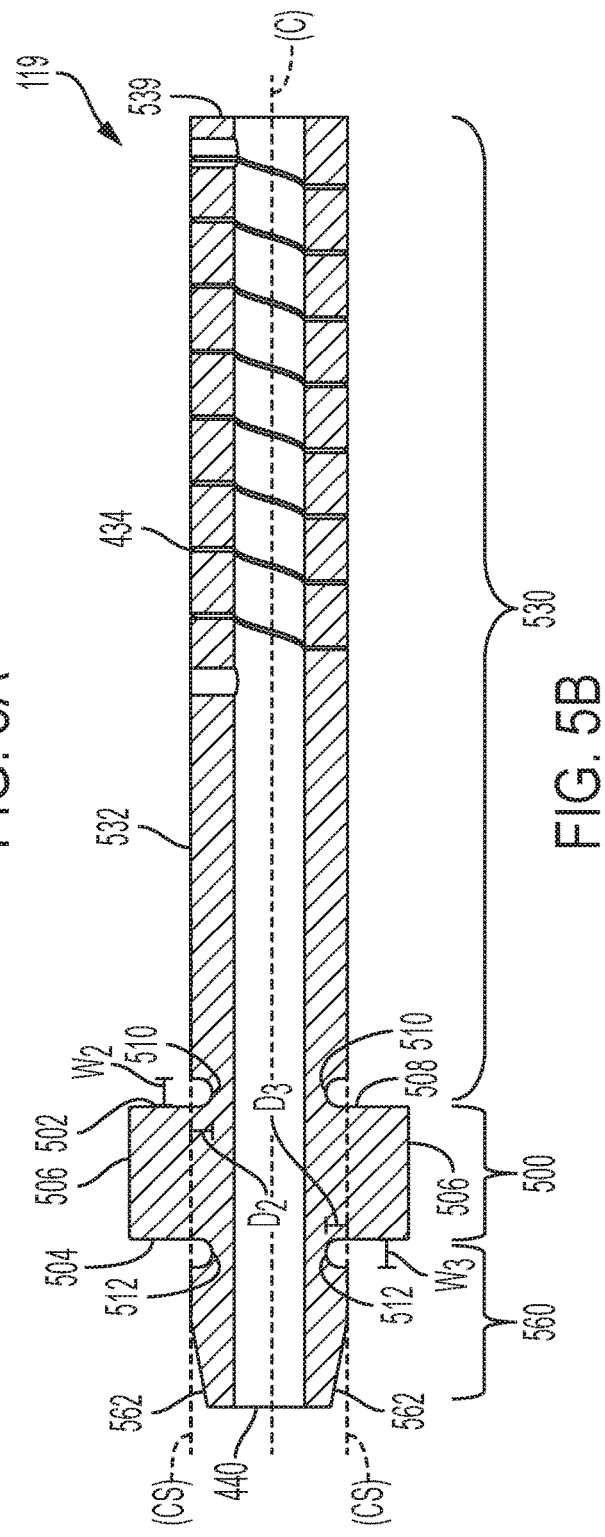

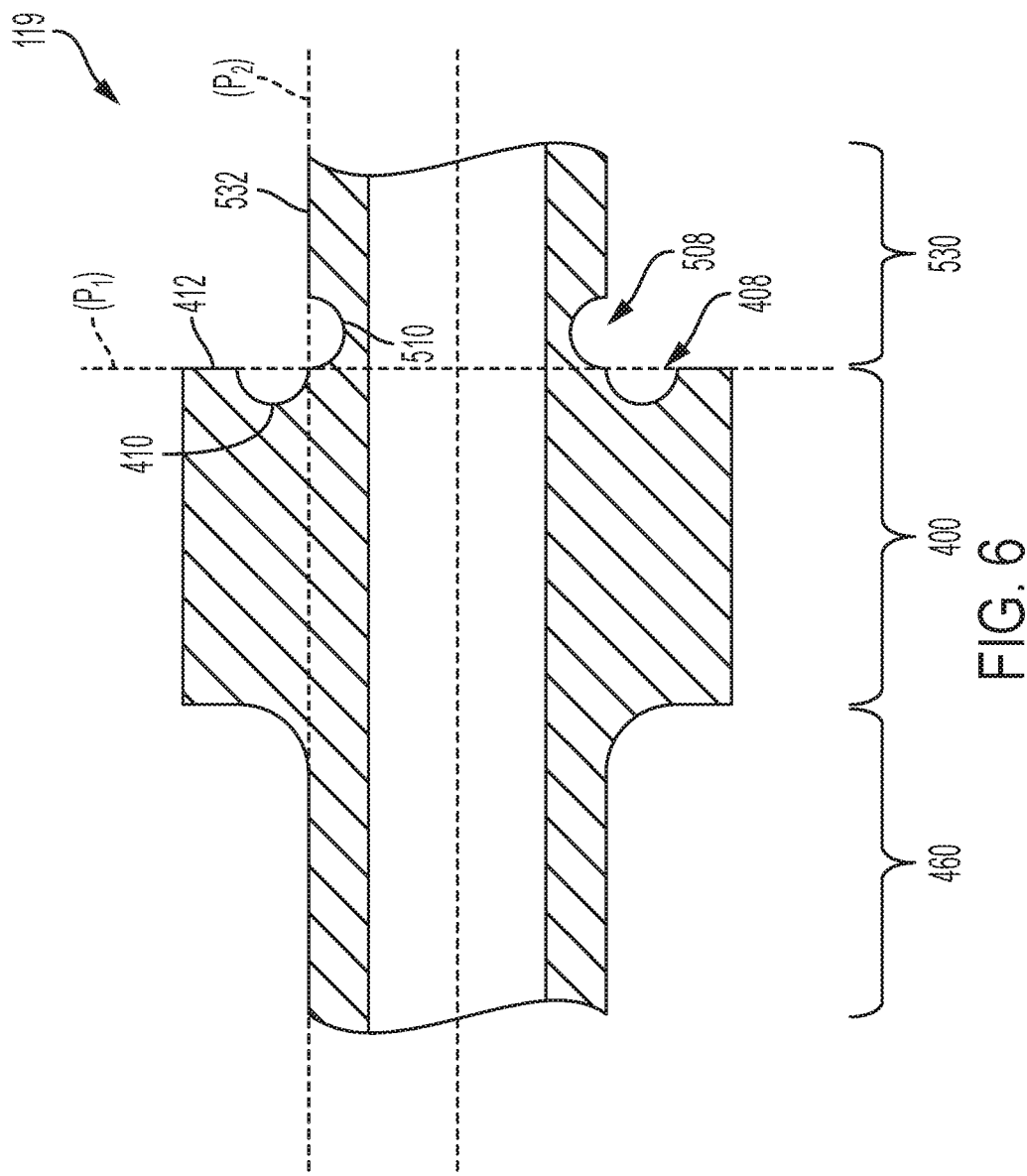

CORE ASSEMBLY FOR MEDICAL DEVICE DELIVERY SYSTEMS

BACKGROUND

Walls of the vasculature, particularly arterial walls, may develop areas of pathological dilatation called aneurysms that often have thin, weak walls that are prone to rupturing. Aneurysms are generally caused by weakening of the vessel wall due to disease, injury, or a congenital abnormality. Aneurysms occur in different parts of the body, and the most common are abdominal aortic aneurysms and cerebral (e.g., brain) aneurysms in the neurovasculature. When the weakened wall of an aneurysm ruptures, it can result in death, especially if it is a cerebral aneurysm that ruptures.

Aneurysms are generally treated by excluding or at least partially isolating the weakened part of the vessel from the arterial circulation. For example, conventional aneurysm treatments include: (i) surgical clipping, where a metal clip is secured around the base of the aneurysm; (ii) packing the aneurysm with small, flexible wire coils (micro-coils); (iii) using embolic materials to "fill" an aneurysm; (iv) using detachable balloons or coils to occlude the parent vessel that supplies the aneurysm; and (v) intravascular stenting.

Intravascular stents are well known in the medical arts for the treatment of vascular stenoses or aneurysms. Stents are prostheses that expand radially or otherwise within a vessel or lumen to support the vessel from collapsing. Methods for delivering these intravascular stents are also well known.

Conventional methods of introducing a compressed stent into a vessel and positioning it within an area of stenosis or an aneurysm include percutaneously advancing a distal portion of a guiding catheter through the vascular system of a patient until the distal portion is proximate the stenosis or aneurysm. A second, inner catheter and a guidewire within the inner catheter are advanced through the distal portion of the guiding catheter. The guidewire is then advanced out of the distal portion of the guiding catheter into the vessel until the distal portion of the guidewire carrying the compressed stent is positioned at the point of the lesion within the vessel. The compressed stent is then released and expanded so that it supports the vessel at the point of the lesion.

SUMMARY

The present technology is illustrated, for example, according to various aspects described below. Various examples of aspects of the present technology are described as numbered clauses (1, 2, 3, etc.) for convenience. These are provided as examples and do not limit the present technology. It is noted that any of the dependent clauses may be combined in any combination, and placed into a respective independent clause, e.g., Clause 1, Clause 50, Clause 86 or Clause 91. The other clauses can be presented in a similar manner.

1. A stent delivery system, comprising:
    a core assembly sized for insertion into a corporeal lumen, the core assembly comprising—
        an elongate member having a distal segment; and
        a proximal restraint coupled to or extending over the distal segment of the elongate member, the proximal restraint including—
            a bumper section;
            an elongate distal section distal to the bumper section;
            a lumen extending through the bumper section and the distal section; and
            an undercut section at least partially surrounding the lumen.

2. The system of Clause 1, wherein the undercut section is configured to inhibit or prevent a proximal end portion of a stent disposed over the distal section from traveling proximally beyond the proximal restraint and/or radially away from a central longitudinal axis of the proximal restraint.

3. The system of any one of Clauses 1 or 2, wherein the bumper section includes a first radial outer surface and the distal section includes a second radial outer surface, and wherein the undercut section is positioned radially between the first radial outer surface and the second radial outer surface.

4. The system of any one of Clauses 1-3, wherein the undercut section is radially peripheral to the distal section.

5. The system of any one of Clauses 1-4, wherein the bumper section includes a distal end portion facing distally and including the undercut section.

6. The system of Clause 5, wherein the distal end portion includes a surface defining a plane substantially orthogonal to a central longitudinal axis of the proximal restraint, wherein at least a portion of the undercut section is proximal to the plane.

7. The system of Clause 5, wherein the distal end portion includes a surface defining a plane substantially orthogonal to a central longitudinal axis of the proximal restraint, wherein a proximalmost point of the undercut section is proximal of the plane.

8. The system of Clause 5, wherein the distal end portion includes a first region comprising the undercut section, and a second region peripheral to the first region and including a surface defining a plane, wherein a portion of the undercut section is proximally beyond the plane.

9. The system of any one of Clauses 6-8, wherein the portion or proximalmost point of the undercut section is separated from the plane by at least about 0.01 millimeters.

10. The system of any one of Clauses 6-9, wherein the undercut section includes a recess or divot extending circumferentially around the lumen.

11. The system of any one of Clauses 1-9, wherein the undercut section comprises a recess formed in the bumper section.

12. The system of Clause 11, wherein the bumper section comprises a distal end surface, and wherein the recess is formed in the distal end surface such that the recess defines a portion of the distal end surface.

13. The system of any one of Clauses 11 or 12, wherein the recess has a depth of from about 0.05-0.1 millimeters.

14. The system of any one of Clauses 11-13, wherein the recess has a depth of at least about 0.05 millimeters.

15. The system of any one of Clauses 11-14, wherein the recess has a width of from about 0.05-0.1 millimeters.

16. The system of any one of Clauses 11-14, wherein the recess has a width of at least about 0.05 millimeters.

17. The system of any one of Clauses 1 or 2, wherein the undercut section is longitudinally between the bumper section and the distal section.

18. The system of any one of Clauses 1, 2 or 17, wherein a first end of the undercut section abuts the bumper section and a second opposing end of the undercut section abuts the distal section.

19. The system of any one of Clauses 1, 2, 17 or 18, wherein the bumper section includes a distal end portion, and wherein the undercut section abuts the distal end portion and is longitudinally between the distal end portion and the distal section.

20. The system of any one of Clauses 1, 2, or 17-19, wherein the distal section includes an outer surface defining a circumferential plane, and wherein a portion of the undercut section is disposed inwardly of the plane.

21. The system of any one of Clauses 1, 2 or 17-19, wherein the distal section includes an outer surface defining a plane, and wherein an innermost point of the undercut section is closer to a central longitudinal axis of the proximal restraint than the plane.

22. The system of any one of Clauses 20 or 21, wherein the portion or innermost point of the undercut section is separated from the plane by at least about 0.01 millimeters.

23. The system of any one of Clauses 20-22, wherein the undercut section includes a recess or divot extending inwardly from the plane and/or circumferentially around the lumen.

24. The system of any one of Clauses 1, 2 or 17-23, wherein the undercut section comprises a recess formed in the distal section.

25. The system of Clause 24, wherein the distal section comprises a radial outer surface, and wherein the recess is formed in the radial outer surface.

26. The system of Clause 25, wherein the recess is formed in the radial outer surface at a proximalmost region of the radial outer surface.

27. The system of any one of Clauses 24-26, wherein the recess has a depth of from about 0.05-0.1 millimeters.

28. The system of any one of Clauses 24-26, wherein the recess has a depth of at least about 0.05 millimeters.

29. The system of any one of Clauses 24-28, wherein the recess has a width of from about 0.05-0.1 millimeters.

30. The system of any one of Clauses 1, 2 or 17-29 wherein the undercut section is a first undercut section, and wherein the proximal restraint further comprises:
   a proximal section proximal to the bumper section, and
   a second undercut section longitudinally between the proximal section and the bumper section.

31. The system of Clause 30, wherein the first and second undercut sections are substantially identical.

32. The system of any one of Clauses 30 or 31, wherein a first end of the second undercut section abuts a proximal end portion of the bumper section and a second opposing end of the second undercut section abuts the proximal section of the proximal restraint.

33. The system of any one of Clauses 30-32, further comprising a longitudinally extending tube having a lumen and a helical cut extending along the tube, the tube being coupled to the proximal section of the proximal restraint.

34. The system of any one of Clauses 10, 11, 23, or 24, wherein the recess or divot includes (a) a curved surface, (b) sidewalls and a base surface extending between the sidewalls, or (c) sidewalls converging toward one another to form a conical or pyramidal recess or divot.

35. The system of any one of Clauses 1-34, wherein the distal section comprises a spacer.

36. The system of any one of Clauses 1-35, wherein the bumper section and the distal section comprise an integrally formed single component.

37. The system of any one of Clauses 1-36, wherein the bumper section and the distal section comprise a continuous surface extending along an entire length of the bumper section and distal section.

38. The system of any one of Clauses 1-37, wherein the bumper section and the distal section comprise separately formed components.

39. The system of any one of Clauses 1-38, wherein the distal section includes a helical cut extending along at least a portion of the length of the distal section.

40. The system of Clause 39, wherein the helical cut extends along only a portion of the length of the distal section.

41. The system of Clause 39, wherein a proximal end of the helical cut is at an intermediate portion of the length of the distal section.

42. The system of Clause 39, wherein a distal end of the helical cut is at an intermediate portion of the length of the distal section.

43. The system of Clause 39, wherein the helical cut extends along the entire length of the distal section.

44. The system of any one of the Clauses 1-43, wherein the elongate member is fixedly attached to the proximal restraint via at least one of welding or adhesive.

45. The system of any one of Clauses 1-44, further comprising a longitudinally-extending tube coupled and proximal to the proximal restraint, the tube having a lumen and a helical cut extending along the tube.

46. The system of any one of Clauses 1-45, wherein the system further comprises a catheter having a lumen configured to receive the core assembly therethrough.

47. The system of any one of Clauses 1-46, wherein the bumper section has a radially outermost dimension of between about 0.55 millimeters and about 0.80 millimeters, and wherein the distal section has a radially outermost dimension of between about 0.25 millimeters and about 0.50 millimeters.

48. The system of any one of Clauses 1-47, wherein the distal section has a length of between about 0.5 millimeters and about 2.5 millimeters.

49. The system of any one of Clauses 1-48, further comprising a stent including a mesh or plurality of intertwined braided filaments.

50. The system of any one of Clauses 1-49, wherein the distal segment of the elongate member extends through the lumen.

51. A proximal restraint for a medical device delivery system, comprising:
   a bumper section having a first cross-sectional dimension;
   a distal section distal to the bumper section and having a second cross-sectional dimension less than the first cross-sectional dimension;
   a lumen extending through the bumper and distal sections; and
   a recess formed in at least one of the bumper or distal sections.

52. The proximal restraint of Clause 51, wherein the recess is configured to inhibit or prevent a proximal end portion of a stent disposed over the distal section from traveling proximally beyond the proximal restraint or radially away from a central longitudinal axis of the proximal restraint.

53. The proximal restraint of any one of Clauses 51 or 52, wherein the bumper section includes a distal end surface, and wherein the recess is formed in the distal end surface.

54. The proximal restraint of any one of Clauses 51-53, wherein the first cross-sectional dimension corresponds to a first radial outer surface and the second cross-sectional dimension corresponds to a second radial outer surface, wherein the recess is radially between the first and second radial outer surfaces.

55. The proximal restraint of any one of Clauses 51-54, wherein the recess is radially peripheral to the distal section.

56. The proximal restraint of any one of Clauses 51-55, wherein the bumper section comprises a distal end portion including a surface defining a plane substantially orthogonal to a central longitudinal axis of the proximal restraint, wherein a portion of the recess is proximal to the plane.

57. The proximal restraint of Clause 56, wherein the portion of the recess is separated from the plane by at least about 0.01 millimeters.

58. The proximal restraint of any one of Clauses 52-57, wherein the recess has a depth of from about 0.01-0.1 millimeters.

59. The proximal restraint of any one of Clauses 52-58, wherein the recess has a depth of at least about 0.01 millimeters.

60. The proximal restraint of any one of Clauses 52-59, wherein the recess has a width of from about 0.01-0.1 millimeters.

61. The proximal restraint of any one of Clauses 51 or 52, wherein the second cross-sectional dimension of the distal section corresponds to an outermost surface, and wherein the recess is formed in the outermost surface.

62. The proximal restraint of any one of Clauses 51-61, wherein the recess is longitudinally between the bumper and distal sections.

63. The proximal restraint of any one of claims 51-62, wherein the bumper section includes a distal end surface, and wherein a proximal end of the recess abuts the distal end surface.

64. The proximal restraint of any one of Clauses 51-63, wherein the distal section comprises a surface defining a plane substantially aligned with a central longitudinal axis of the proximal restraint, wherein a portion of the recess is inward of the plane.

65. The proximal restraint of Clause 64, wherein the portion of the recess is separated from the plane by at least about 0.01 millimeters.

66. The proximal restraint of any one of Clauses 51-65, wherein the recess has a depth of from about 0.01-0.1 millimeters.

67. The proximal restraint of any one of Clauses 51-66, wherein the recess has a depth of at least about 0.01 millimeters.

68. The proximal restraint of any one of Clauses 51-67, wherein the recess has a width of from about 0.01-0.1 millimeters.

69. The proximal restraint of any one of Clauses 51-68, wherein the recess is a first recess, and wherein the proximal restraint further comprises:
   a proximal section proximal to the bumper section, and
   a second recess longitudinally between the proximal section and the bumper section.

70. The proximal restraint of Clause 69, wherein the first and second recesses are substantially identical.

71. The proximal restraint of any one of Clauses 69 or 70, wherein a first end of the second recess abuts a proximal end portion of the bumper section and a second opposing end of the second recess abuts the proximal section of the proximal restraint.

72. The proximal restraint of any one of Clauses 69-71, further comprising a longitudinally-extending tube having a lumen and a helical cut extending along the tube, the tube being coupled to the proximal section of the proximal restraint.

73. The proximal restraint of any one of Clauses 51-72, wherein the recess includes (a) a curved surface, (b) sidewalls and a base surface extending between the sidewalls, or (c) sidewalls converging toward one another to form a conical or pyramidal recess.

74. The proximal restraint of any one of Clauses 51-73, wherein the distal section comprises a spacer.

75. The proximal restraint of any one of Clauses 51-74, wherein the bumper section and the distal section comprise an integrally formed single component.

76. The proximal restraint of any one of Clauses 51-75, wherein the bumper section and the distal section comprise a continuous surface extending along an entire length of the bumper section and distal section.

77. The proximal restraint of any one of Clauses 51-76, wherein the bumper section and the distal section comprise separately formed components.

78. The proximal restraint of any one of Clauses 51-77, wherein the distal section includes a helical cut.

79. The proximal restraint of Clause 78, wherein the helical cut extends along only a portion of the length of the distal section.

80. The proximal restraint of Clause 78, wherein a proximal end of the helical cut is at an intermediate portion of the length of the distal section.

81. The proximal restraint of Clause 78, wherein a distal end of the helical cut is at an intermediate portion of the length of the distal section.

82. The proximal restraint of Clause 78, wherein the helical cut extends along the entire length of the spacer.

83. The proximal restraint of any one of Clauses 51-82, further comprising a stent engagement member distal to the distal section and including two or more projections.

84. The proximal restraint of any one of Clauses 51-83, further comprising:
   a first engagement member distal to the distal section;
   a first spacer distal to the first engagement member;
   a second engagement member spaced apart from the first engagement member by the first spacer.

85. The proximal restraint of any one of Clauses 51-84, wherein the first cross-sectional dimension corresponds to a radially outermost dimension of between about 0.55 millimeters and about 0.80 millimeters, and wherein the second cross-sectional dimension corresponds to a radially outermost dimension of between about 0.55 millimeters and about 0.50 millimeters.

86. The proximal restraint of any one of Clauses 51-85, wherein the distal section has a length of between about 0.5 millimeters and about 2.5 millimeters.

87. The proximal restraint of any one of Clauses 51-86, wherein the lumen is configured to receive an elongate core member.

88. A medical device delivery system, comprising:
   a core assembly sized for insertion into a corporeal lumen, the core assembly comprising the proximal restraint of any one of Clauses 50-85.

89. The medical device delivery system of Clause 88, further comprising an elongate member having a distal segment extending through the lumen of the proximal restraint.

90. The medical device delivery system of any one of Clauses 88 or 89, further comprising a stent disposed around the distal section of the proximal restraint.

91. The medical device delivery system of any one of Clauses 88-90, further comprising a catheter including a lumen configured to receive the core assembly therethrough.

92. The medical device delivery system of Clause 91, wherein the catheter is a first catheter configured to guide the core assembly through vasculature of a patient, the medical device delivery system further comprising a second catheter disposed within the first catheter.

93. A method of operating a medical device delivery system, the method comprising:
inserting a core assembly into a lumen of a catheter, the core assembly comprising—
an elongate member;
the proximal restraint of any one of Clauses 50-85; and
a stent distal to the proximal restraint and extending longitudinally over at least a portion of the elongate member; and
advancing the core assembly through the catheter.

94. The method of Clause 93, wherein advancing the core assembly comprises contacting a proximal end of the stent with a distally facing portion of the bumper section.

95. The method of any one of Clauses 93 or 94, wherein, while advancing the core assembly, a proximal end of the stent is at least partially received within the recess.

96. The method of any one of Clauses 93-95, wherein advancing the core assembly comprises distally advancing the core assembly such that at least a portion of the stent is allowed to extend out of the core assembly and expand.

97. The method of Clause 96, further comprising proximally retracting the elongate member prior to releasing the stent such that the stent is recaptured to within the lumen of the catheter.

98. A method of operating a medical device delivery system, comprising:
inserting a core assembly into a lumen of a catheter, the core assembly comprising—
an elongate member;
a restraint including a bumper section, a distal section distal to the bumper section, a lumen extending through the bumper and distal sections; and
a stent distal to the restraint and extending longitudinally over at least a portion of the elongate member;
advancing the core assembly through the catheter; and
via the configuration of an interface between the bumper section and the distal section, preventing a proximal end of the stent from being deflected radially outward by the interface.

99. The method of Clauses 98, wherein the bumper section has an outer diameter of 0.030 inches or less.

100. The method of any one of Clauses 98 or 99, wherein the distal section has an outer diameter of 0.020 inches or less.

101. The method of any one of Clauses 99-100, wherein the bumper section projects radially beyond an outer diameter of the distal section by a distance of 0.007 to 0.015 inches.

102. The method of Clause 98, further comprising a recess extending at least partially around the lumen, wherein at least one of the bumper or distal sections includes the recess.

103. The method of Clause 98, wherein advancing the core assembly comprises contacting a proximal end portion of the stent with a distally facing portion of the bumper section.

104. A proximal restraint for a medical device delivery system, comprising:
a bumper section having a first outer diameter and a distal end defining a radial plane;
an elongate distal section distal to the bumper section and having a second outer diameter less than the first outer diameter, the distal section defining a longitudinal cylindrical surface; and
a lumen extending through the bumper and distal sections; and
a radially non-spreading interface located where the radial plane and the longitudinal cylindrical surface meet.

105. The restraint of Clause 104, wherein the first outer diameter is 0.030 inches or less.

106. The restraint of any one of Clauses 104 or 105, wherein the second outer diameter is 0.020 inches or less.

107. The restraint of any one of Clauses 104-106, wherein the bumper section projects radially beyond the second outer diameter by a distance of 0.007 to 0.015 inches.

108. The restraint of any one of Clauses 104-107, further comprising a recess extending at least partially around the lumen, the recess positioned at or adjacent to the location where the radial plane and the longitudinal cylindrical surface meet.

109. The restraint of Clause 108, wherein at least one of the bumper or distal sections includes the recess.

110. A stent delivery system comprising:
the restraint of any one of Clauses 51-87 or 104-109;
an elongate member, wherein the restraint is coupled to or positioned on the elongate member; and
a stent having a proximal end positioned adjacent to or against the distal end of the bumper section.

Additional features and advantages of the present technology will be set forth in the description below, and in part will be apparent from the description, or may be learned by practice of the subject technology. The advantages of the present technology will be realized and attained by the structure particularly pointed out in the written description and claims hereof as well as the appended drawings.

It is to be understood that both the foregoing general description and the following detailed description are exemplary and explanatory and are intended to provide further explanation of the present technology as claimed.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present technology. For ease of reference, throughout this disclosure identical reference numbers may be used to identify identical or at least generally similar or analogous components or features.

FIG. 2A is a side view of the core assembly of the medical device delivery system shown in FIG. 1.

FIG. 2B is a side, cross-sectional view of the core assembly of FIG. 2A.

FIG. 4A is an isometric view of an embodiment of the proximal restraint shown in FIG. 3.

FIG. 4B is a side, cross-sectional view of the proximal restraint shown in FIG. 4A.

FIG. 5A is an isometric view of an embodiment of the proximal restraint shown in FIG. 3.

FIG. 5B is a side, cross-sectional view of the proximal restraint shown in FIG. 5A.

FIG. 6 is a side, cross-sectional view of an embodiment of the proximal restraint shown in FIG. 3.

DETAILED DESCRIPTION

Figure 1:
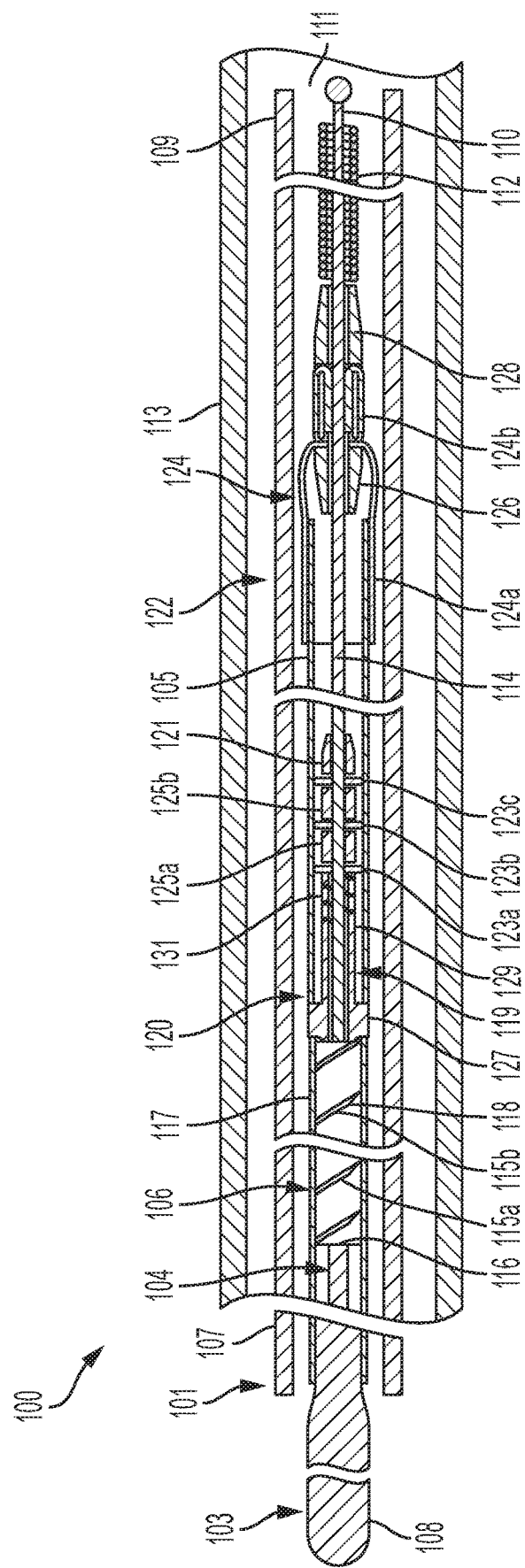
FIG. 1 is a side, cross-sectional view of a medical device delivery system, according to some embodiments of the present technology.

Conventional medical device delivery systems may include a core member or core assembly configured to carry a medical device (e.g., a stent) through a catheter. The core assembly can include an elongate member, a proximal restraint coupled to the elongate member, and a stent distal to the proximal restraint and carried by the elongate member. When the core assembly carrying the stent is distally advanced through a catheter lumen (or when a surrounding catheter is proximally retracted relative to the core assembly and stent), the proximal end of the stent may abut the proximal restraint. The proximal restraint can be configured to "push" the stent and also to prevent the stent from traveling proximal thereof. In some embodiments, the proximal restraint can include a bumper portion having an outer profile that is larger than that of the stent when the stent is in a compressed state. As the stent is distally advanced through a patient's vasculature, e.g., toward a target site, the stent is urged relatively proximally toward the proximal restraint and generally inhibited from traveling proximally therebeyond due to the larger outer profile of the bumper portion.

Despite this intended general use of the proximal restraints, proximal restraints are susceptible to the limitations and/or defects of manufacturing that can limit some of their functionality. For example, due in part to the small size of the proximal restraint in many vascular applications, the interface of a radially-extending distal end face of the bumper portion and an adjacent longitudinally-extending cylindrical surface may be unintentionally rounded, as opposed to forming a geometrically precise 90° (or less) corner when viewed in a sectional plane coincident with a longitudinal axis of the delivery system. As such, when the stent is urged relatively proximally toward the proximal restraint, the rounded surface can act as an outward-leading ramp and cause the proximally-projecting filament ends (or strut ends) of the stent to "ride up" the proximal face of the bumper in a radial direction, possibly enabling the stent to travel proximally beyond the proximal restraint, thereby damaging a surrounding catheter and/or preventing delivery of the stent altogether.

Embodiments of the present technology provide an improved core assembly and/or proximal restraint that reduces the risk of such issues. For example, embodiments of the present technology can comprise a proximal restraint including an undercut portion having a recess. As described in more detail below, the undercut portion or recess can be configured to inhibit or prevent the stent or other interventional element from traveling proximally beyond the proximal restraint, which can damage the catheter or cause a failure of delivery.

Specific details of several embodiments of the present technology are described herein with reference to FIGS. 1-6. Although many of the embodiments are described with respect to devices, systems, and methods for delivery of stents and other medical devices, other applications and other embodiments in addition to those described herein are within the scope of the present technology. Further, embodiments of the present technology can have different configurations, components, and/or procedures than those shown or described herein. Moreover, embodiments of the present technology can have configurations, components, and/or procedures in addition to those shown or described herein and these and other embodiments may not have several of the configurations, components, and/or procedures shown or described herein without deviating from the present technology.

As used herein, the terms "distal" and "proximal" define a position or direction with respect to a clinician or a clinician's control device (e.g., a handle of a delivery catheter). For example, the terms, "distal" and "distally" refer to a position distant from or in a direction away from a clinician or a clinician's control device along the length of device. In a related example, the terms "proximal" and "proximally" refer to a position near or in a direction toward a clinician or a clinician's control device along the length of device. The headings provided herein are for convenience only and should not be construed as limiting the subject matter disclosed.

FIGS. 1-6 depict embodiments of medical device delivery systems that may be used to deliver and/or deploy a medical device, such as but not limited to a stent, into a hollow anatomical structure such as a blood vessel. The stent can comprise a braided stent or other form of stent such as a woven stent, knit stent, laser-cut stent, roll-up stent, etc. The stent can optionally be configured to act as a "flow diverter" device for treatment of aneurysms, such as those found in blood vessels including arteries in the brain or within the cranium, or in other locations in the body such as peripheral arteries. The stent can optionally be similar to any of the versions or sizes of the PIPELINE™ Embolization Device marketed by Medtronic Neurovascular of Irvine, Calif. USA. The stent can alternatively comprise any suitable tubular medical device and/or other features as described herein. In some embodiments, the stent can be any one of the stents described in U.S. application Ser. No. 15/892,268, filed Feb. 8, 2018, titled VASCULAR EXPANDABLE DEVICES, the entirety of which is hereby incorporated by reference herein and made a part of this specification.

FIG. 1 is a side cross-sectional view of a medical device delivery system 100 configured in accordance with embodiments of the present technology. The delivery system 100 can be configured to carry a stent (or other vascular implant or device) 105 thereon to be advanced through a surrounding elongate tube or catheter 101 to a target site in a patient, for example, a site within a corporeal lumen 113 such as a blood vessel. The catheter 101 can slidably receive a core member or core assembly 103 configured to carry the stent 105 thereon. The depicted catheter 101 has a proximal portion 107 and an opposing distal portion 109 which can be positioned at a treatment site within a patient, and an internal lumen 111 extending from the proximal portion 107 to the distal portion 109. At the distal portion 109, the catheter 101 has a distal opening through which the core assembly 103 may be advanced beyond the distal portion 109 to expand or deploy the stent 105 within the corporeal lumen 113. The proximal portion 107 may include a catheter hub (not shown). The catheter 101 can define a generally longitudinal dimension extending between the proximal portion 107 and the distal portion 109. When the delivery system 100 is in use, the longitudinal dimension need not be straight along some or any of its length.

The delivery system 100 can be used with any number of catheters. For example, the catheter 101 can optionally comprise any of the various lengths of the MARKSMAN™ catheter available from Medtronic Neurovascular of Irvine, Calif. USA. The catheter 101 can optionally comprise a microcatheter having an inner diameter of about 0.030 inches or less, and/or an outer diameter of 3 French or less near the distal portion 109. Instead of or in addition to these specifications, the catheter 101 can comprise a microcatheter which is configured to percutaneously access the internal carotid artery, or another location within the neurovasculature distal of the internal carotid artery.

The core assembly 103 can generally comprise any member(s) with sufficient flexibility and column strength to move the stent 105 or other medical device through the catheter 101. For example, the core assembly 103 can comprise a wire, tube (e.g., hypotube), braid, coil, or other suitable member(s), or a combination of wire(s), tube(s), braid(s), coil(s), etc. The embodiment of the core assembly 103 depicted in FIG. 1 is of a multi-member construction, comprising a longitudinally extending member, shaft or elongate member 104 and an elongate tube 106 surrounding at least a portion of the elongate member 104. An outer layer 117, which can comprise a layer of lubricious material such as PTFE (polytetrafluoroethylene), TEFLON™ or other lubricious polymer, can cover some or all of the tube 106 and/or the elongate member 104.

The elongate member 104 has a proximal portion 108 and a distal portion 110, which can optionally include a tip coil 112. The elongate member 104 can be constructed from materials including polymers and metals including nitinol and stainless steels. In some embodiments, the elongate member 104 tapers in the distal direction, having a larger diameter at the proximal portion 108 and a smaller diameter at the distal portion 110. The taper may be gradual and continuous along the length of the elongate member 104, or in some embodiments the taper may vary at different portions of the elongate member 104. As described in more detail below, in some embodiments the elongate member 104 can include one or more constant-diameter segments in which the elongate member 104 does not taper. Such constant-diameter segments can be useful, e.g., for utilizing a single wire in combination with tubes 106 and/or stents 105 of different lengths.

The elongate member 104 can also include an intermediate portion 114 located between the proximal portion 108 and the distal portion 110. The intermediate portion 114 includes the portion of the core assembly 103 onto or over which the stent 105 extends when the core assembly 103 is in the pre-deployment configuration as shown in FIG. 1. The elongate member 104 may include one or more fluorosafe markers (not shown), and such marker(s) can be located on a portion of the elongate member 104 that is not covered by the outer layer 117 (e.g., proximal of the outer layer 117). This portion of the elongate member 104 marked by the marker(s), and/or proximal of any outer layer 117, can comprise a bare metal outer surface.

The tube 106 extends from a proximal portion 116 to a distal portion 118 and surrounds the elongate member 104 along at least a portion of the length of the elongate member 104. In some embodiments, the distal portion 118 of the tube 106 terminates proximal to the intermediate portion 114 of the elongate member 104, such that during operation, the stent 105 is carried by the intermediate portion 114 of the elongate member 104 at a position distal to the tube 106.

The tube 106 can have a sidewall that is "uncut" or without openings or voids formed therein. Alternatively, the tube 106 can have openings, voids, and/or cuts formed in the sidewall, e.g., to enhance the flexibility of the tube. The openings, voids and/or cuts can be formed by (a) cutting a series of slots in the sidewall along part or all of the length of the tube 106, (b) cutting or drilling a pattern of other openings in the sidewall, or (c) cutting a spiral-shaped void or helical cut in the sidewall. For example, as shown in FIG. 1, the tube 106 has a helically extending void or cut 115 in the sidewall that extends from the proximal portion 116 to the distal portion 118. The cut 115 can include multiple segments having different pitches, for example the first segment 115a can have a lower pitch than the second segment 115b. By varying the pitch in different segments of the cut 115, the bending stiffness of the tube 106 can be precisely tailored along the length of the tube 106. Although two segments of the cut 115 are illustrated in FIG. 1, the tube 106 can have a large number of different segments (e.g., three segments, five segments, etc.) each having different pitch dimensions.

In some embodiments, for example where the delivery system is to be used in narrow and/or tortuous vasculature, such as the neurovasculature, the tube 106 can include a relatively small outside diameter (e.g., 0.040" or less, or 0.030" or less, or 0.027" or less, or about 0.020", or about 0.016"). In some embodiments, the outer diameter of the tube 106 can be configured to substantially fill the lumen 111 of the catheter 101. As used herein, "fill" means that an outer diameter of the tube 106 extends substantially across the internal diameter of the lumen 111 of the catheter 101. In some embodiments, the tube 106 fills at least about 50%, 60%, 70%, 80%, 90%, or more of the lumen 111 of the catheter 101.

The tube 106 can have a relatively thin sidewall thickness (e.g., 80 microns or less, 70 microns or less, 60 microns or less, or 50 microns or less, or between about 50 and 60 microns). The tube 106 can also have a relatively long overall length (e.g., 400 mm or more, 500 mm or more, 600 mm or more, 700 mm or more, 800 mm or more, between about 400 and 600 mm, or about 514 mm). Instead of or in addition to any one or combination of such dimensions, the tube 106 can have a relatively long cut length (the length of the portion of the tube 106 in which opening(s), void(s), spiral(s), or cut(s) 115 is/are present) of 400 mm or more, 500 mm or more, 600 mm or more, 700 mm or more, 800 mm or more, or about 514 mm.

A relatively long, small-diameter, and/or thin-walled spiral-cut tube offers certain advantages for use in the core assembly 103 in narrow and/or tortuous vasculature, such as the neurovasculature. The tube 106 can be made highly flexible (or inflexible as the case may be) where necessary by use of an appropriate spiral pitch. In addition to or in lieu of the foregoing, the column strength or "pushability" of the tube 106 can be maintained largely independent of its flexibility, as the diameter of the tube 106 can remain constant along its length. The combination of high flexibility and pushability can facilitate easier navigation into difficult, tortuous vascular locations.

In various embodiments of the tube 106, the helical or spiral cut 115 can be relatively long and continuous. For example, the tube 106 can have such a helical or spiral cut 115 over any of the various cut lengths specified above or elsewhere herein for the tube 106. A tube 106 having such a helical or spiral cut 115 can also have any one or combination of the various outside diameters, sidewall thicknesses, and/or overall lengths specified above or elsewhere herein for the tube 106. The helical or spiral cut can extend along the entire length of the tube, or nearly the entire length, e.g. the entire length except for a small uncut portion at the distal and/or proximal end, as shown in FIG. 2A with regard to the distal end where the spiral cut is terminated with a stress relief hole.

The long contiguous or continuous helical or spiral cut 115 can be implemented using any number of techniques. In some embodiments, two or more longitudinally adjacent spirals, cuts, slots or voids can be formed contiguously or continuously in the sidewall of the tube 106 and joined at their adjacent ends by connection aperture(s) to form a spiral or helical cut, slot, or void that is contiguous or continuous along the overall length or along the cut length of the tube 106. In some embodiments, the individual spirals, cuts, slots, or voids can be about 150 mm in length, or 150 mm or less in length. These need not be uniform in length along the tube or cut length. For example, the first or last spiral cut, slot, or void can be made relatively shorter in order to achieve a cut length that is not an even multiple of the length of the individual spirals.

In some embodiments, one or more terminal apertures may be employed in the spiral or helical cut, slot, or void. In still other embodiments of the tube 106, a spiral or helical cut, slot, or void is employed with terminal aperture(s) at one or both terminal ends and no connecting apertures along the cut length. One or multiple such spirals may be formed in the sidewall of a single tube 106. Where employed, the terminal aperture(s) can serve as a stress relief or measure against sidewall crack formation at the end(s) of the spiral.

Instead of or in addition to a spiral cut 115 that is contiguous or continuous over a relatively long overall length or cut length of the tube 106, the pitch of the spiral can be controlled precisely over a long overall length or cut length. For example, the pitch of the spiral cut 115 can vary over the cut length such that a pitch of a specific magnitude can prevail along a relatively short segment of the cut length, for example 5 mm or less, 3 mm or less, 2 mm or less, or about 1.0 mm. In this manner, the spiral pitch can be finely adjusted in small increments of the cut length thereby facilitating superior control over the mechanical properties of the tube 106 (e.g., bending stiffness, column strength) in various portions of the tube. Therefore, the tube 106 can have a pitch that varies in magnitude (including a specific "first pitch magnitude") along the overall length or cut length of the tube, and the first pitch magnitude can prevail along a first segment of the cut length. The first segment can have a length (measured along the longitudinal dimension of the tube 106) of 5 mm or less, 3 mm or less, 2 mm or less, or about 1 mm. The magnitude of the pitch can change from the first magnitude at one or both ends of the first segment. The first segment can be located (e.g., in a contiguous or continuous void) anywhere along the cut length, including location(s) relatively far from the endpoints of the cut length, e.g., more than 100 mm away, more than 200 mm away, or more than 300 mm away from an endpoint of the cut length.

Instead of or in addition to achievement of a particular pitch magnitude in one or more short segments of the cut length (and/or a spiral that is contiguous or continuous over a relatively long overall length or cut length of the tube 106), the pitch magnitude can be controlled precisely so that it can vary in relatively small increments. (The pitch can be expressed in mm/rotation.) For example, the pitch can vary in magnitude by 0.2 mm/rotation or less, 0.1 mm/rotation or less, 0.01 mm/rotation or less, or 0.005 mm/rotation or less. This provides another manner in which the spiral can be finely controlled to facilitate desired mechanical properties in various portions of the tube 106. Therefore, the tube 106 can have a pitch that varies in magnitude (including a specific "first pitch magnitude") along the overall length or cut length of the tube, and the first pitch magnitude can prevail along a first segment of the cut length. The magnitude of the pitch can change from the first magnitude by 0.2 mm/rotation or less, 0.1 mm/rotation or less, 0.01 mm/rotation or less, or 0.005 mm/rotation or less, at one or both ends of the first segment. The first segment can be located (e.g., in a contiguous or continuous void) anywhere along the cut length, including location(s) relatively far from the endpoints of the cut length, e.g., more than 100 mm away, or more than 200 mm away, or more than 300 mm away from an endpoint of the cut length.

As described in more detail below, the tube 106 can be mounted over the elongate member 104 such that the tube 106 is affixed to the elongate member 104. For example, the tube 106 can be affixed to the elongate member 104 at one or more contact points. In one embodiment, the tube 106 is affixed to the elongate member 104 at one or more contact points in the proximal portion 116 and at one or more contact points in the distal portion 118 of the tube 106. The tube 106 can be affixed to the elongate member 104 at these contact points by soldering, welding, adhesive, or other suitable fixation technique. In some embodiments, there may be two, three, four, or more contact points at which the tube 106 is affixed to the elongate member 104. In other embodiments, the tube 106 may be affixed to the elongate member 104 at only a single contact point. In still other embodiments, the tube 106 may not be affixed to the elongate member 104. As used herein, "affixed" includes both direct and indirect fixation, for example, the elongate member 104 can be directly welded or adhered to the tube 106 at a contact point, or the tube can be welded or otherwise attached to an intervening member (e.g., the proximal restraint), which in turn is affixed directly to the elongate member 104.

Affixing portions of the tube 106 to the elongate member 104 can reduce or eliminate elongation or compression of the tube 106 during operation of the delivery system 100. As noted above, the relatively large diameter of the tube 106 can enhance pushability of the core assembly 103. However, the presence of flexibility enhancing cuts (e.g., the helical cut 115 extending along the length of the tube) may cause the tube 106 to elongate or compress during movement of the core assembly 103 with respect to the catheter 101. For example, during distal advancement of the core assembly 103, the distal portion 118 of the tube 106 may resist movement (for example, due to frictional engagement with an inner wall of the catheter 101) more than the proximal portion 116 of the tube 106. As a result, the proximal portion 116 and the distal portion 118 would move closer towards one another, resulting in compression of the tube 106 and a reduction in overall length. If instead the distal portion 118 of the tube 106 resisted proximal movement to a greater degree than the proximal portion 116, then the proximal portion 116 and the distal portion 118 would move further apart, resulting in elongation of the tube 106 and an increase in its overall length. Both elongation and compression can disadvantageously alter the performance characteristics of the tube 106, and therefore the core assembly 103. For example, elongation or compression can modify the flexibility, column strength, and navigability of the core assembly 103. By affixing the tube 106 to the underlying elongate member 104 at one or more contact points, the risk of compression or elongation of the tube 106 can be reduced. In some embodiments, proximal and distal ends of the tube 106 can be affixed to the elongate member 104, thereby effectively fixing the overall length of the tube 106 and substantially eliminating compression or elongation of the tube 106 during operation of the delivery system 100. In other embodiments, the tube 106 can be affixed to the elongate member 104 at contact points that are spaced apart from proximal and distal ends of the tube 106, such as intermediate portions of the tube 106.

The system 100 can also include a coupling assembly 120 or resheathing assembly 120 configured to releasably retain the medical device or stent 105 with respect to the core assembly 103. The coupling assembly 120 can be configured to engage the stent 105, e.g., via mechanical interlock with the pores and filaments of the stent 105, abutment of the proximal end or edge of the stent 105, frictional engagement with the inner wall of the stent 105, or any combination of these modes of action. The coupling assembly 120 can therefore cooperate with the overlying inner surface of the catheter 101 to grip and/or abut the stent 105 such that the coupling assembly 120 can move the stent 105 along and within the catheter 101. For example, distal and/or proximal movement of the core assembly 103 relative to the catheter 101 can result in a corresponding distal and/or proximal movement of the stent 105 within the catheter lumen 111.

The coupling assembly 120 (or portion(s) thereof) can, in some embodiments, be configured to rotate about the core assembly 103. In some such embodiments, the coupling assembly 120 can comprise a proximal restraint 119 and a distal restraint 121. The proximal and distal restraints 119, 121 can be fixed to the core assembly 103 to prevent or limit proximal or distal movement of the coupling assembly 120 along the longitudinal dimension of the core assembly 103. For example, one or both of the proximal and distal restraints 119, 121 can be soldered or fixed, e.g., with adhesive, to the elongate member 104. One or both of the proximal and distal restraints 119, 121 can have an outside diameter or other radially outermost dimension that is smaller than the outside diameter or other radially outermost dimension of the overall coupling assembly 120 such that an outer profile of one or both of the restraints 119, 121 is positioned radially inward of the inner surface of the stent 105 during operation of the system 100. In some embodiments, the proximal restraint 119 can be sized to abut the proximal end of the stent 105, e.g., to prevent or inhibit the stent from traveling distally thereof during delivery. The proximal and distal restraints 119, 121 can comprise a metal such as platinum, iridium, gold, tungsten or combinations thereof (e.g., 90% platinum/10% iridium).

The proximal restraint 119 can include a bumper section 127 and a distal section 129 that extends distally from the bumper section 127. As described in more detail below, the distal section 129 can be a tubular member having a helical cut extending along at least a portion of its length, thereby forming a proximal spiral-cut section 131. In some embodiments, the proximal spiral-cut section 131 and the proximal restraint 119 can be formed as an integrally formed, single component such that the proximal spiral-cut section 131 comprises part of the proximal restraint 119. In other embodiments, the proximal spiral-cut section 131 can be formed individually, separate from the proximal restraint 119 and coupled thereto. In operation, the stent 105 may extend over the distal section 129 of the proximal restraint 119, such that a proximal end of the stent 105 abuts the bumper section 127 of the proximal restraint 119. As the coupling assembly 120 is distally advanced through the lumen 111 of the catheter 109 (or as the catheter 109 is proximally retracted relative to the coupling assembly 120), the bumper section 127 of the proximal restraint 119 can "push" the stent 105 or otherwise inhibit or prevent relative proximal movement of the stent 105 proximally beyond the bumper section 127 of the proximal restraint 119.

The coupling assembly 120 can also include one, two, three or more stent engagement members (or device engagement members, or resheathing members) and one, two or more spacers disposed about the core assembly 103 between the proximal and distal restraints 119, 121. In the illustrated embodiment, the coupling assembly 120 includes first, second and third stent engagement members 123a-c (collectively referred to as "engagement members 123") and first and second spacers 125a-b (collectively referred to as "spacers 125") disposed over the elongate member 104. In a distal direction, the elements of the coupling assembly 120 include the proximal restraint 119, the first stent engagement member 123a, the first spacer 125a, the second stent engagement member 123b, the second spacer 125b, the third stent engagement member 123c and the distal restraint 121. The first spacer 125a defines the relative longitudinal spacing between the first engagement member 123a and the second engagement member 123b, and the second spacer 125b defines the relative longitudinal spacing between the second engagement member 123b and the third engagement member 123c.

The stent engagement members 123 and the spacers 125 (or any of the engagement members or spacers disclosed herein) can be fixed to the elongate member 104 so as to be immovable relative to the elongate member 104, in a longitudinal/sliding manner and/or in a radial/rotational manner. Alternatively, the spacers 125 and/or the stent engagement members 123 can be coupled to (e.g., mounted on) the elongate member 104 so that the spacers 125 and/or the stent engagement members 123 can rotate about the longitudinal axis of the elongate member 104, and/or move or slide longitudinally along the core member 103. In such embodiments, the spacers 125 and/or the stent engagement members 123 can each have an inner lumen or aperture that receives the elongate member 104 therein such that the spacers 125 and/or the stent engagement members 123 can slide and/or rotate relative to the elongate member 104.

In some embodiments, the proximal and distal restraints 119, 121 can be spaced apart along the core member 103 by a longitudinal distance that is slightly greater than the combined length of the spacers 125 and the stent engagement members 123, so as to leave one or more longitudinal gaps between the individual spacers 123, engagement members 125, and/or proximal and distal restraints 119, 121, When present, the longitudinal gap(s) allow the spacers 125 and/or the stent engagement members 123 to slide longitudinally along the elongate member 104 between the restraints 119, 121. The longitudinal range of motion of the spacers 125 and the stent engagement members 123 between the restraints 119, 121 is approximately equal to the total combined length of the longitudinal gap(s), if any. In some embodiments, the combined length of the longitudinal gap(s) between the proximal restraint 119 and the distal restraint 121 can be 0.05 mm or less. In various embodiments, such longitudinal gap(s) can facilitate rotatability of the engagement members 123 and/or spacers 125 about the elongate member 104. Such longitudinal gaps(s) can also improve bendability of the core member 103 and the coupling unit 121 about a relatively sharp radius of curvature, as may be required when navigating the tortuous anatomy of a patient's neurovasculature.

One or both of the spacers 125 can take the form of a wire coil, a solid tube, or other structural element that can be mounted over the core assembly 103 to longitudinally separate adjacent components of the coupling assembly 120. In some embodiments, one or both of the spacers 125 can be a zero-pitch coil with flattened ends. In some embodiments, one or both of the spacers 125 can be a solid tube (e.g., a laser-cut tube) that can be rotatably mounted or non-rotatably fixed (e.g., soldered) to the core assembly 103. The spacers 125 can have a radially outermost dimension that is smaller than a radially outermost dimension of adjacent components, e.g., the engagement members 123 such that the spacers 125 do not contact the stent 105 during normal operation of the system 100. The dimensions, construction, and configuration of the spacers 125 can be selected to achieve improved grip between the coupling assembly 120 and the overlying stent 105.

The stent 105 can be moved distally or proximally within the overlying catheter 101 via the proximal coupling assembly 120. In some embodiments, the stent 105 can be resheathed via the proximal coupling assembly 120 after partial deployment of the stent 105 from a distal opening of the catheter. In embodiments in which the proximal restraint 119 is sized to abut the proximal end of the stent 105 and employed to push the stent distally during delivery, the first and second stent engagement members 123a-b can be employed to resheath the stent 105 after partial deployment, while taking no (or substantially no) part in pushing the stent distally during delivery. For example, the first and second stent engagement members 123a-b can in such embodiments transmit no, or substantially no, distal push force to the stent 105 during delivery.

Optionally, the proximal edge of the proximal coupling assembly 120 can be positioned just distal of the proximal edge of the stent 105 when in the delivery configuration. In some such embodiments, this enables the stent 105 to be re-sheathed when as little as a few millimeters of the stent remains in the catheter. Therefore, with stents of typical length, resheathability of 75% or more can be provided (i.e. the stent can be re-sheathed when 75% or more of it has been deployed).

With continued reference to FIG. 1, the distal interface assembly 122 can comprise a distal engagement member 124 that can take the form of, for example, a distal device cover or distal stent cover (generically, a "distal cover"). The distal cover 124 can be configured to reduce friction between the stent 105 (e.g., a distal portion thereof) and the inner surface of the surrounding catheter 101. For example, the distal cover 124 can be configured as a lubricious, flexible structure having a free first end or section 124a that can extend over at least a portion of the stent 105 and/or intermediate portion 108 of the core assembly 103, and a fixed second end or section 124b that can be coupled (directly or indirectly) to the core assembly 103.

The distal cover 124 can have a first or delivery position, configuration, or orientation in which the distal cover can extend proximally relative to the distal tip, or proximally from the second section 124b or its (direct or indirect) attachment to the core assembly 103, and at least partially surround or cover a distal portion of the stent 105. The distal cover 124 can be movable from the first or delivery orientation to a second or resheathing position, configuration, or orientation (not shown) in which the distal cover can be everted such that the first end 124a of the distal cover is positioned distally relative to the second end 124b of the distal cover 124 to enable the resheathing of the core assembly 103, either with the stent 105 carried thereby, or without the stent 105. As shown in FIG. 1, the first section 124a of the distal cover 124 can originate from the proximal end of the second section 124b. In another embodiment, the first section 124a can originate from the distal end of the second section 124b.

The distal cover 124 can be manufactured to include a lubricious and/or hydrophilic material such as PTFE or Teflon®, but may be made from other suitable lubricious materials or lubricious polymers. The distal cover can also comprise a radiopaque material which can be blended into the main material (e.g., PTFE) to impart radiopacity. The distal cover 124 can have a thickness of between about 0.0005" and about 0.003". In some embodiments, the distal cover can be one or more strips of PTFE having a thickness of about 0.001".

The distal cover 124 (e.g., the second end 124b thereof) can be fixed to the core assembly 103 (e.g., to the elongate member 104 or distal tip thereof) so as to be immovable relative to the core assembly 103, either in a longitudinal/sliding manner or a radial/rotational manner. Alternatively, as depicted in FIG. 1, the distal cover 124 (e.g., the second end 124b thereof) can be coupled to (e.g., mounted on) the core assembly 103 so that the distal cover 124 can rotate about a longitudinal axis of the core assembly 103 (e.g., of the elongate member 104), and/or move or slide longitudinally along the core assembly 103. In such embodiments, the second end 124b can have an inner lumen that receives the core assembly 103 therein such that the distal cover 124 can slide and/or rotate relative to the core assembly 103. Additionally, in such embodiments, the distal interface assembly 122 can further comprise a proximal restraint 126 that is fixed to the core assembly 103 and located proximal of the (second end 124b of the) distal cover 124, and/or a distal restraint 128 that is fixed to the core assembly 103 and located distal of the (second end 124b of the) distal cover 124. The distal interface assembly 122 can comprise a radial gap between the outer surface of the core assembly 103 (e.g., of the elongate member 104) and the inner surface of the second end 124b. Such a radial gap can be formed when the second end 124b is constructed with an inner luminal diameter that is somewhat larger than the outer diameter of the corresponding portion of the core assembly 103. When present, the radial gap allows the distal cover 124 and/or second end 124b to rotate about the longitudinal axis of the core assembly 103 between the proximal and distal restraints 126, 128.

In some embodiments, one or both of the proximal and distal restraints 126, 128 of the distal interface assembly 122 can have an outside diameter or other radially outermost dimension that is smaller than the (e.g., pre-deployment) outside diameter or other radially outermost dimension of the distal cover 124, so that one or both of the restraints 126, 128 will tend not to bear against or contact the inner surface of the catheter during operation of the core assembly 103. Alternatively, it can be preferable to make the outer diameters of the restraints 126 and 128 larger than the largest radial dimension of the pre-deployment distal cover 124, and/or make the outer diameter of the proximal restraint 126 larger than the outer diameter of the distal restraint 128. This configuration allows easy and smooth retrieval of the distal cover 124 and the restraints 126, 128 back into the catheter post stent deployment.

In operation, the distal cover 124, and in particular the first section 124a, can generally cover and protect a distal portion of the stent 105 as the stent 105 is moved distally through a surrounding catheter. The distal cover 124 may serve as a bearing or buffer layer that, for example, inhibits filament ends of the distal portion of the stent 105 (where the stent comprises a braided stent) from contacting an inner surface of the catheter, which could damage the stent 105 and/or catheter, or otherwise compromise the structural integrity of the stent 105. Since the distal cover 124 may be made of a lubricious material, the distal cover 124 may exhibit a low coefficient of friction that allows the distal portion of the stent to slide axially within the catheter with relative ease. The coefficient of friction between the distal cover 124 and the inner surface of the catheter 101 can be between about 0.02 and about 0.4. For example, in embodiments in which the distal cover and the catheter are formed from PTFE, the coefficient of friction can be about 0.04. Such embodiments can advantageously improve the ability of the core assembly 103 to pass through the catheter, especially in tortuous vasculature.

Structures other than those embodiments of the distal cover 124 described herein may be used in the core assembly 103 and/or distal interface assembly 122 to cover or otherwise interface with the distal portion of the stent 105. For example, a protective coil or other sleeve having a longitudinally oriented, proximally open lumen may be employed. In other embodiments, the distal interface assembly 122 can omit the distal cover 124, or the distal cover can be replaced with a component similar to the proximal coupling assembly 120. Where the distal cover 124 is employed, it can be connected to the distal tip coil 112 (e.g., by being wrapped around and enclosing some or all of the winds of the coil 112) or being adhered to or coupled to the outer surface of the coil by an adhesive or a surrounding shrink tube. The distal cover 124 can be coupled (directly or indirectly) to other portions of the core assembly 103, such as the elongate member 104.

In embodiments of the core assembly 103 that employ both a rotatable proximal coupling assembly 120 and a rotatable distal cover 124, the stent 105 can be rotatable with respect to the core assembly 103 about the longitudinal axis thereof, by virtue of the rotatable connections of the proximal coupling assembly 120 and distal cover 124. In such embodiments, the stent 105, proximal coupling assembly 120, and distal cover 124 can rotate together in this manner about the core assembly 103. When the stent 105 can rotate about the core assembly 103, the core assembly 103 can be advanced more easily through tortuous vessels as the tendency of the vessels to twist the stent 105 and/or core assembly 103 is negated by the rotation of the stent 105, proximal coupling assembly 120, and distal cover 124 about the core assembly 103. In addition, the required push force or delivery force is reduced, as the user's input push force is not diverted into torsion of the stent 105 and/or core assembly 103. The tendency of a twisted stent 105 and/or core assembly 103 to untwist suddenly or "whip" upon exiting tortuosity or deployment of the stent 105, and the tendency of a twisted stent to resist expansion upon deployment, are also reduced or eliminated. Further, in some such embodiments of the core assembly 103, the user can "steer" the core assembly 103 via the tip coil 112, particularly if the coil 112 is bent at an angle in its unstressed configuration. Such a coil tip can be rotated about a longitudinal axis of the system 100 relative to the stent 105, coupling assembly 120 and/or distal cover 124 by rotating the distal portion 110 of the core assembly 103. Thus the user can point the coil tip 112 in the desired direction of travel of the core assembly 103, and upon advancement of the core assembly the tip will guide the core assembly in the chosen direction.

FIG. 2A is a side view of the core assembly 103 of the medical device delivery system 100 shown in FIG. 1, and FIG. 2B is a side cross-sectional view of the core assembly 103 of FIG. 2A taken along line 2B-2B. As noted above, the core assembly 103 includes an elongate shaft or elongate member 104 and a longitudinally extending tube 106 that surrounds the elongate member 104 along at least a portion of the length of the elongate member 104. The elongate member 104 includes a proximal portion 108, a distal portion 110, and an intermediate portion 114 configured to carry the stent 105 (FIG. 1) thereon. The tube 106 is disposed over the elongate member 104 such that the elongate member 104 extends through an inner lumen of the tube 106. The elongate member 104 can have a length greater than a length of the tube 106, such that the elongate member 104 extends proximal to the proximal portion 116 of the tube 106 and also extends distal to the distal portion 118 of the tube 106.

As noted above, the tube 106 can have a spiral or helical void or cut 115 extending along at least a portion of the length of the tube 106, and the cut 115 can include one or more segments 115a-b having the same pitch dimensions or different pitch dimensions to impart varying bending stiffness to different portions of the tube 106 along its length. As shown in the illustrated embodiment, the first segment 115a of the cut 115 includes a first pitch and the second segment 115b of the cut 115 includes a differing second pitch (e.g., a higher pitch). In some embodiments, the pitch of the cut 115 can decrease proximally, e.g., to enable additional bending at distal portions of the tube 106. The cut 115 can terminate in an aperture 232 formed in the sidewall of the tube 106. The aperture 232 can comprise an additional void that is formed (e.g., cut) in the sidewall of the tube 106 and is contiguous or continuous with the void or cut 115. The aperture 232 can comprise a circle, as shown in FIG. 2A, or any other suitable shape such as an ellipse or polygon. When employed, the aperture 232 can serve as a stress relief or measure against sidewall crack formation at the end of the helical cut 115. In some embodiments, different segments of the cut 115 (e.g., first segment 115a and second segment 115b) can be connected by connection apertures, thereby forming a single, contiguous, and/or continuous void. The connection apertures can be substantially similar to the aperture 232, except that they are positioned between adjacent segments of the cut 115 (e.g., between the first segment 115a and the second segment 115b).

The elongate member 104 can have an outer profile that tapers radially inwardly in the distal direction, thereby having a larger outer profile (e.g., diameter) at the proximal portion 108 and a smaller outer profile at the distal portion 110. The taper may be gradual and continuous along the length of the elongate member 104, or in some embodiments the taper may vary at different portions of the elongate member 104. In the embodiment illustrated in FIGS. 2A and 2B, the elongate member 104 can include two (or more) constant-diameter segments, such as a first constant-diameter segment 234 and a second constant-diameter segment 236. Over each of these segments 234, 236, the elongate member 104 can have a substantially uniform (i.e., non-tapered) outer profile. The first constant-diameter segment 234 can be positioned to underlie the proximal portion 116 of the tube 106, and the second constant-diameter segment 236 can be positioned to underlie the distal portion 118 of the tube 106. Because the elongate member 104 tapers distally from the first constant-diameter segment 234 to the second constant-diameter segment 236, in some embodiments the outer profile (e.g., diameter) of the first constant-diameter segment 234 is greater than the outer profile (e.g., diameter) of the second constant-diameter segment 236. In some embodiments, the first constant-diameter segment 234 can have a length of between about 1" to 8", 2" to 6", 3" to 5", or about 4". In some embodiments, the second constant-diameter segment 236 can likewise have a length of between about 1" to 8", 2" to 6", 3" to 5", or about 4".

The first and second segments 234, 236 can provide portions of the elongate member 104 configured to be affixed to corresponding portions of the surrounding tube 106. The tube 106 can be affixed to the elongate member 104 at a first contact point 238 at the proximal portion 116 of the tube 106, and can also be affixed to the elongate member 104 at the second contact point 240 at the distal portion 118 of the tube 106. The first contact point 238 can be positioned at any longitudinal position within the first constant-diameter segment 234, and the second contact point 240 can be positioned at any longitudinal position within the second constant-diameter segment 236. Accordingly, the first and second constant-diameter segments 234, 236 enable the elongate member 104 to accommodate the first and second contact points 238, 240 at a range of different longitudinal positions within the first and second constant-diameter segments, 234, 236, respectively. For example, in various embodiments, the first contact point 238 can be positioned at any longitudinal position along the length of the first constant-diameter segment 234, and the second contact point 240 can be positioned at any longitudinal position along the length of the second constant-diameter segment 236.

This feature can be useful for utilizing a single configuration of the elongate member 104 in combination with tubes 106 and/or stents 105 (FIG. 1) of different lengths. For example, the intermediate portion 114 of the elongate member 104 may accommodate stents having a range of different stent sizes. In the case of longer stents, the proximal end of the stent may extend more proximally along the wire than with a shorter stent. To position the proximal restraint 119 adjacent to the proximal end of the stent, the restraint 119 may be placed at different longitudinal positions along the second constant-diameter segment 236 depending on the length and position of the stent. With a shorter stent, the restraint 119 (along with the distal portion 118 of the tube 106) will be positioned more distally than with a longer stent. By moving the restraint 119 and the distal portion 118 of the tube 106 along the second constant-diameter segment 236, the proximal portion 116 of the tube 106 is also moved along the first constant-diameter segment 234 by an equivalent amount. Accordingly, the lengths of the first and second constant-diameter segments 234, 236 can provide a range of longitudinal positions over which the first and second contact points 238, 240 can be located.

The elongate member 104 and the tube 106 can be configured such that, during operation of the delivery system, the tube 106 preferentially bends before the elongate member 104. For example, the sidewall thickness, material section, and helical cut 115 of the tube 106 can all be varied to provide the desired bending stiffness at different portions along the length of the tube 106. Likewise, the material and dimensions of the elongate member 104 can be varied along the length of the elongate member 104 to provide varied bending stiffness along its length. The relative bending stiffnesses of the elongate member 104 and the tube 106 can be configured such that, when bending the core assembly 103 (for example, during navigation of tortuous anatomy), the tube 106 bends before the elongate member 104. This allows strain to be borne primarily by the tube 106, which can reduce the load borne by the elongate member 104 and decrease the required delivery force.

As noted above, the tube 106 can be affixed to the elongate member 104 along the first constant-diameter segment 234 at a first contact point 238. For example, the first contact point 238 can be at the proximalmost end of the tube 106. The elongate member 104 can be affixed to the tube 106 at the first contact point 238 via welding, soldering, adhesive, or any other suitable fixation technique. The outer profile (e.g., diameter) of the elongate member 104 can be configured to facilitate fixation of the elongate member 104 to the tube 106 at the first contact point 238. For example, in some embodiments, the outer profile of the elongate member 104 is nearly as large as the inner profile of the lumen of the tube 106, such that the elongate member 104 substantially fills the lumen of the tube 106 at the first contact point 238. This can facilitate welding, soldering, or otherwise affixing or attaching the elongate member 104 to the tube 106. As the outer profile of the tube 106 can be substantially constant along the first constant-diameter segment 234, the tube 106 can be affixed to the elongate member 104 at the first contact point 238 at any point along the length of the first constant-diameter segment 234.

In some embodiments, the tube 106 can be affixed to the restraint 119 along the second constant-diameter segment 236 at a second contact point 240. For example, the proximal restraint 119 can be mounted over the elongate member 104 at a longitudinal position within the second constant-diameter segment 236 of the elongate member 104. In some embodiments, the tube 106 can be affixed to the restraint 119 at the second contact point 240 via welding, soldering, adhesive, or any other suitable fixation technique. The outer profile (e.g., diameter) of the restraint 119 can be configured to facilitate fixation of the restraint 119 to the tube 106 at the second contact point 240. For example, in some embodiments, the outer profile of the proximal section 444 of the restraint 119 is nearly as large as the inner profile of the lumen of the tube 106, such that the proximal portion 444 of the restraint 119 substantially fills the lumen of the tube 106 at the second contact point 240. This can facilitate welding, soldering, or otherwise affixing or attaching the restraint 119 to the tube 106.

In some embodiments, the tube 106 can be affixed directly to the elongate member 104 at the second contact point 240, for example via welding, soldering, adhesive, or other fixation technique. In some embodiments, instead of the restraint 119, the tube 106 can be connected to another intervening member which in turn is attached to the elongate member 104. For example, an attachment member separate from the restraint 119 can be affixed to the elongate member 104, and the tube 106 can in turn be affixed to the attachment member at the second contact point 240.

In some embodiments, the elongate member 104 may include only the first constant-diameter segment 234 and omit the second constant-diameter segment 236, while in other embodiments the elongate member 104 may include only the second constant-diameter segment 236 and omit the first constant-diameter segment. In still other embodiments, the elongate member 104 may omit both the first and second constant-diameter segments 234, 236, instead having a tapering or otherwise varying outer profile in those segments of the elongate member 104.

Although the first and second contact points 238, 240 are shown as being at or near proximal and distal ends of the tube 106, in some embodiments one or more of the first and second contact points 238, 240 can be located at positions spaced apart from the proximal and distal ends of the tube 106. Additionally or alternatively, in some embodiments there may be additional contact points located at other longitudinal locations along the elongate member 104. For example, an additional contact point can be provided between the first and second contact points 238, 240, thereby providing another point of fixation between the tube 106 and the elongate member 104 and further preventing compression or elongation of the tube 106 with respect to the wire.

As previously described, the proximal restraint 119 can inhibit or prevent the stent 105 from traveling proximally beyond the proximal restraint 119 during delivery of the stent 105. As shown in the illustrated embodiment of FIG. 3, for example, the proximal restraint 119 can include a bumper section 300, a distal section 330 distal to the bumper section 300, and a proximal section 360 proximal to the bumper section 300. The bumper section 300 includes an outer profile (e.g., outer diameter) equal to or larger than that of the stent 105, and a distal end face 310 configured to abut and stop the stent 105 from traveling proximally therebeyond. The distal end face 310 can meet an adjacent surface 312 of the distal section 330 of the proximal restraint 119 to form a corner (e.g., 90° or less angle) at their interface when viewed in a sectional longitudinal plane that is coincident with a longitudinal axis of the core assembly 103. In practice, manufacturing the proximal restraint 119 to include such a corner can be difficult, e.g., due to the small size of proximal restraint 119, or more particularly the limited interface between the distal end face 310 and adjacent surface 312. Due in part to these limitations and/or difficulties, manufacturing of the proximal restraint 119 may unintentionally create the interface with a concave, rounded or curved surface, rather than a geometrically precise right angle (or other angle around 90°, or less) which may be less able to inhibit or prevent the stent 105 from traveling proximally beyond the proximal restraint 119. For example, such a curved surface may form a sort of ramp and enable the proximal end of the stent 105 to "ride up" the distal end face 310 of the bumper section 300 of the proximal restraint 119. This can involve the distal end of the stent 105 moving radially outward, abrading the inner wall of the surrounding catheter, and/or preventing further delivery of the stent 105. As described herein, embodiments of the present technology can mitigate this issue, e.g., by including an undercut section and/or recess configured to inhibit or prevent a proximal end portion of the stent 105 from traveling proximally beyond the proximal restraint 119.

Figure 3:
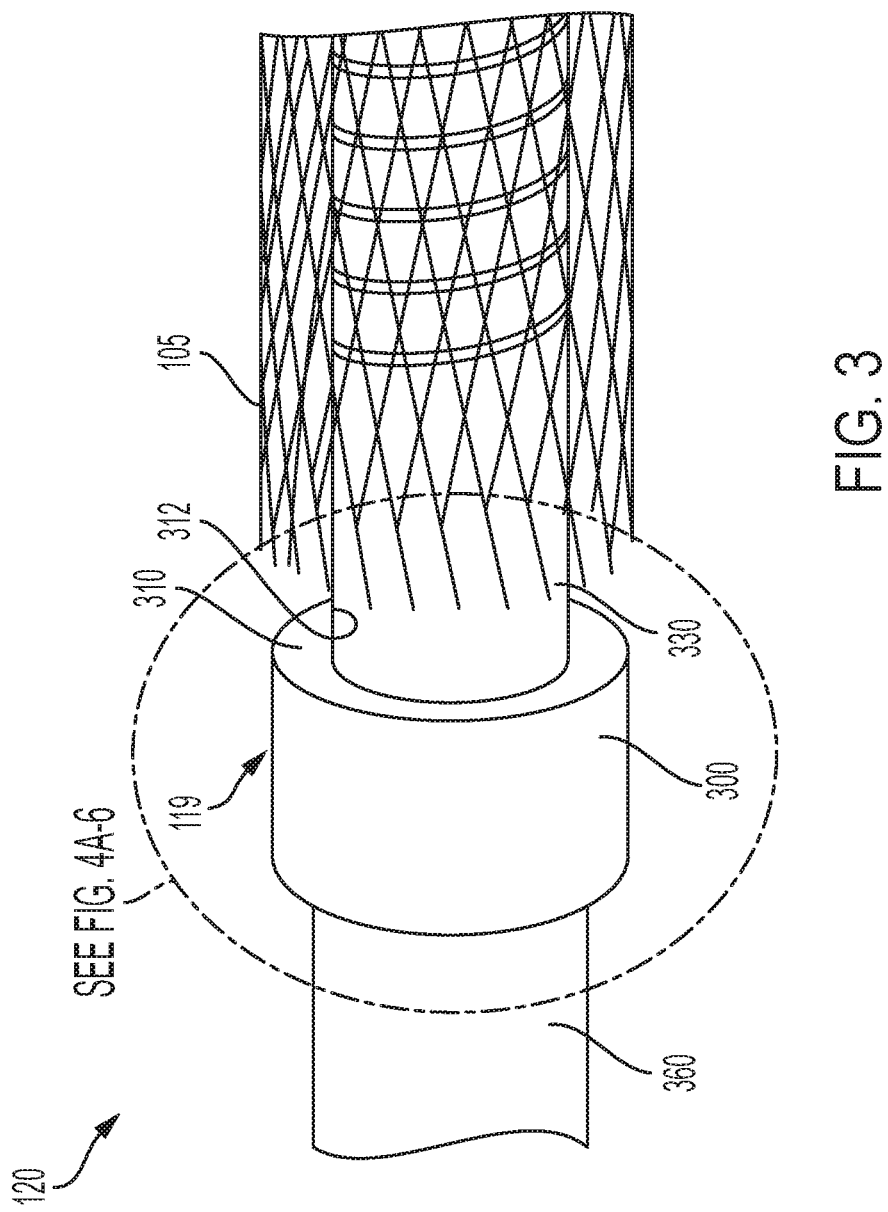
FIG. 3 is an isometric view of a portion of the core assembly shown in FIG. 2A.

FIG. 3, as well as FIGS. 4A-6, depict various embodiments of proximal restraints for use with a medical device delivery system. They can be used with any of the embodiments of the delivery systems shown in FIGS. 1 and 2, or with any other medical device delivery systems. Such other medical device delivery systems may include any one or multiple features in common with the delivery systems of FIGS. 1 and 2, or may include no such common features.

FIG. 4A is an isometric view of an embodiment of the proximal restraint 119 shown in FIG. 3, and FIG. 4B is a side, cross-sectional view of the proximal restraint 119 shown in FIG. 4A taken along line 4B-4B. Referring to FIGS. 4A and 4B together, the proximal restraint 119 can include a bumper section 400, a distal section 430 distal to the bumper section 400, a proximal section 460 proximal to the bumper section 400, a lumen 440 extending longitudinally through the proximal, bumper and distal sections 460, 400, 430, and an undercut section 408. In some embodiments, two or more of the proximal, bumper and distal sections 460, 400, 430 of the proximal restraint 119 can be an integrally formed single component. In such embodiments, the proximal restraint 119 can include a continuous surface extending along an entire length of the proximal restraint 119 or portion thereof having the integrally formed components. In some embodiments, the proximal, bumper and distal sections 460, 400, 430 can be formed separately (e.g., not as an integrally formed single component), and be individually coupled to one another, e.g., via adhesive, welding, soldering, threaded engagement or other attachment method(s).

The bumper section 400 can include a distal end portion 402 (FIG. 4A), a proximal end portion 404 (FIG. 4A), and an outer profile 406 (e.g., outer surface, outer diameter, or outer cross-sectional dimension) extending longitudinally between the distal and proximal end portions 402, 404. The bumper section 400 can include the undercut section 408 (FIG. 4B) having a recess or divot 410 relative to an abutting surface. As shown in FIGS. 4A and 4B, for example, the distal end portion 402 can include a distal end surface 412, and the recess 410 can be formed in the distal end surface 412. The distal end surface 412 can define a plane (Pi) (e.g., a radial plane), and the recess 410 or a portion thereof can extend proximally beyond the plane (Pi). In some embodiments, the plane (Pi) is substantially orthogonal or normal to a central longitudinal axis (C) of the proximal restraint 119 and/or coplanar with the distal end surface 412. As further shown in FIGS. 4A and 4B, the distal section 430 can include an outer profile 432 (e.g., outer surface, outer diameter, or outer cross-sectional dimension), and the recess 410 can be disposed circumferentially around the outer profile 432 such that the recess 410 has a continuous surface surrounding the outer profile 432. Additionally or in lieu of the foregoing, the recess 410 can be disposed circumferentially around the lumen 440 such that the recess 410 has a continuous surface surrounding the lumen 440. In some embodiments, the recess 410 may surround only a portion of the outer profile 432 and/or lumen 440. The recess 410 can form a distally-facing pocket that can receive the proximal end (e.g., the proximally-projecting filament ends or strut ends) of the stent 105 as the stent 105 moves proximally relative to the bumper section 400. This prevents the stent 105 from traveling proximally beyond the proximal restraint 119, and causing damage to the surrounding catheter, while preserving the ability to deliver the stent 105.

The dimensions of the recess 410 can vary, e.g., depending on the particular application of the medical device being delivered to the patient. For example, the recess 410 can include a depth ($D_1$) (e.g., distance from a proximalmost point of the recess 410 to the plane (Pi)) of about 0.1 mm or less, 0.09 mm or less, 0.08 mm or less, 0.07 mm or less, 0.06 mm or less, 0.05 mm or less, or 0.04 mm or less. The recess 410 can include a width ($W_1$) of about 0.1 mm or less, 0.09 mm or less, 0.08 mm or less, 0.07 mm or less, 0.06 mm or less, 0.05 mm or less, or 0.04 mm or less. In some embodiments, the recess 410 can make up a portion of all of the distal end portion 402. For example, the recess 410 can include about 50% or less, 60% or less, 70% or less, 80% or less, 90% or less, or 100% of the length of the distal end portion 402. As shown in FIGS. 4A and 4B, the recess 410 includes a curved surface and, in such embodiments, can include a semi-circular or semi-oval shape. In some embodiments, the recess 410 can include non-curved surfaces and/or other shapes, such as a "box" shape in which the recess 410 includes sidewalls and a flat or non-curved base surface extending between the sidewalls, or a conical, pyramidal or "V" shape in which the recess 410 includes sidewalls that converge toward one another. In some embodiments the bumper section 400 can have an outer diameter of 0.030 inches or less, and the distal section 430 can have an outer diameter of 0.020 inches or less. In addition to or in lieu of the foregoing diameters, the bumper section 400 can project radially beyond the outer diameter of the distal section 430, e.g., by a distance of 0.007 to 0.015 inches. Such dimensions can be useful in some vascular applications such as neurovascular applications.

The distal section 430 can comprise a spacer or other tubular member that includes the outer profile 432 extending longitudinally along a length of the distal section 430. As shown in FIGS. 4A and 4B, the distal section 430 abuts the bumper section 400, or more particularly abuts the undercut section 408 (FIG. 4B) or recess 410 of the bumper section 400. In some embodiments, the distal section 430 may not abut the bumper section 400, undercut section 408 or recess 410. For example, the undercut section 408 and/or recess 410 may be spaced apart (e.g., radially spaced apart) from the distal section 430 such that the undercut section 408 and/or recess 410 is aligned with an outer profile of a stent disposed over the proximal restraint 119. In some embodiments, a spacer or other material may be included between the bumper and distal sections 400, 430.

The distal section 430 can include a helical void or cut 434 extending along an entire length or only a portion of the distal section 430. Features of the cut 434 can include any of the features previously described with reference to cut 115 (FIGS. 1-2B). As shown in FIGS. 4A and 4B, the cut 434 can include a proximalmost point 436 at an intermediate portion (e.g., spaced apart from a proximal end portion) of the distal section 430. That is, the cut 434 extends along only a portion of the length of the distal section 430. In such embodiments, the proximalmost point 436 may, for example, be spaced apart from the plane (Pi) by about 1.0 mm or less, 0.9 mm or less, 0.8 mm or less, 0.7 mm or less, 0.6 mm or less, or 0.5 mm or less. Positioning the proximalmost point 436 of the cut 434 at the intermediate portion of the distal section 430, as opposed to the proximal end portion, can prevent or limit bending at the proximal end portion of the distal section 430. Additionally or in lieu of the foregoing, positioning the proximalmost point 436 at the intermediate portion can decrease the likelihood that braid ends of a stent or mesh component disposed over the proximal restraint 119 become caught or tangled in the cut 434, and/or fall out of engagement with the recess 410. For example, during delivery of a medical device through a patient's vasculature, the distal section 430 will bend along the cut 434, and the braid ends of the stent, which may be loose or frayed, can become caught in the cut 434. By having the proximalmost point 436 of the cut 434 at the intermediate portion, the braid ends of the stent are spaced apart from the cut 434, and thus the likelihood of them becoming caught or tangled is decreased.

The cut 434 can terminate at a distalmost point 438 at a distal portion of the distal section 430. In some embodiments, the distalmost point 438 is spaced apart from the distal terminus 439 (FIG. 4B) of the distal section 430, e.g., by about 0.1 mm or less, 0.09 mm or less, 0.08 mm or less, 0.07 mm or less, 0.06 mm or less, or 0.05 mm or less.

The cut 434 can include a constant pitch or a pitch that varies along a length of the cut 434. For example, the cut 434 can include multiple segments, with one or more of the multiple segments having a different pitch relative to the other segments. In some embodiments, varying the pitch can advantageously allow the distal section 430 to have desirable mechanical properties (e.g., pushability, column strength, and/or bending stiffness). The pitch of the one or more segments can include about 0.2 mm/rotation or less, 0.175 mm/rotation or less, 0.15 mm/rotation or less, 0.125 mm/rotation or less, 0.1 mm/rotation or less, 0.075 mm/rotation or less, or 0.05 mm/rotation or less.

The proximal section 460 of the proximal restraint 119 can include an outer profile 462 (e.g., outer surface, outer diameter or outer dimension) extending along a length of the proximal section 460. In some embodiments, the outer profile 462 has a smaller diameter or dimension than that of the outer profile 406. The proximal section 460 can be configured (e.g., sized) to slidably receive a tubular member thereover, such as tube 106 (FIGS. 1-2B). In such embodiments, the tube 106 can be disposed over the proximal section 460 to abut the bumper section 400. In some embodiments, the proximal section 460 can be configured to substantially fill the lumen of the tube 106, such that the tube 106 is secured to the proximal restraint 119 via friction between the outer profile 462 and inner surface of the tube 106. As shown in FIGS. 4A and 4B, the outer profile 462 includes a constant diameter along a length of the proximal section 460. In some embodiments, the outer profile 462 can taper, e.g., in a proximal direction such that the diameter of the proximal section 460 increases distally.

FIG. 5A is an isometric view of an embodiment of the proximal restraint 119 shown in FIG. 3, and FIG. 5B is a side, cross-sectional view of the proximal restraint 119 shown in FIG. 5A taken along line 5B-5B. Referring to FIGS. 5A and 5B together, the proximal restraint 119 can include a bumper section 500, a distal section 530 distal to the bumper section 500, a proximal section 560 proximal to the bumper section 500, a lumen 440 extending longitudinally through the proximal, bumper and distal sections 560, 500, 530, and an undercut section 508. The bumper section 500 can include a distal end surface 502, a proximal end surface 504, and an outer profile 506 (e.g., outer surface, outer diameter, or outer cross-sectional dimension) extending longitudinally between the distal and proximal end surfaces 502, 504.

In some embodiments, two or more of the proximal, bumper and distal sections 560, 500, 530 of the proximal restraint 119 can be an integrally formed single component. In such embodiments, the proximal restraint 119 can include a continuous surface extending along an entire length of the proximal restraint 119 or portion thereof having the integrally formed components. In some embodiments, two or more of the proximal, bumper and distal sections 560, 500, 530 can be formed separately (e.g., not as an integrally formed single component), and be individually coupled to one another, e.g., via adhesive, welding, soldering, threaded engagement or other attachment method(s).

The distal section 530 can comprise a spacer or other tubular member that includes an outer profile 532 (e.g., outer surface, outer diameter, or outer cross-sectional dimension) extending longitudinally along a length of the distal section 530. The distal section 530 can include the undercut section 508 (FIG. 5A) having a recess or divot 510 (FIG. 5B) relative to an abutting surface. As shown in FIGS. 5A and 5B, the recess 510 is formed in the outer profile 532 at a proximal end portion of the distal section 530. In some embodiments, the outer profile 532 can define a longitudinal cylindrical surface (CS), and the recess 510 or a portion thereof can extend inwardly of the longitudinal cylindrical surface (CS), such that the inwardmost point of the recess 510 is closer to the central longitudinal axis (C) than the longitudinal cylindrical surface (CS) is. In some embodiments, the longitudinal cylindrical surface (CS) is substantially orthogonal to the distal end surface 502. As shown in FIGS. 5A and 5B, the recess 510 is disposed circumferentially in the outer profile 532, and abuts or is contiguous to the distal end surface 502. Stated differently, the recess 510 is disposed circumferentially around the lumen 440 of the proximal restraint 119 such that the recess 510 has a continuous surface circumferentially surrounding the lumen 440. In some embodiments, the recess 510 may surround only a portion of the outer profile 532 and/or lumen 440. The recess 510 effectively "submerges" the rounded portion of the interface between the bumper and the distal section 530 radially below the level of the outer profile 532 or longitudinal cylindrical surface (CS). This eliminates the "ramp" effect and presents a fully orthogonal bumper surface to the stent. This in turn prevents the stent 105 from traveling proximally beyond the proximal restraint 119, and damage to the surrounding catheter, while preserving the ability to deliver the stent 105. As embodiments of the various proximal restraints shown in FIGS. 4A-6 can eliminate this ramp effect, each of them may be considered to provide a radially non-spreading interface between the bumper (e.g. the distal face thereof) and the distal section (e.g. the outer diameter or outer profile thereof).

The dimensions of the recess 510 can vary, e.g., depending on the particular application of the medical device being delivered to the patient. For example, the recess 510 can include a depth ($D_2$) (e.g., outward distance from an inwardmost point of the recess 510 to the longitudinal cylindrical surface (CS)) of about 0.1 mm or less, 0.09 mm or less, 0.08 mm or less, 0.07 mm or less, 0.06 mm or less, 0.05 mm or less, or 0.04 mm or less. The recess 510 can include a width ($W_2$) (e.g., longitudinal length) of about 0.1 mm or less, 0.09 mm or less, 0.08 mm or less, 0.07 mm or less, 0.06 mm or less, 0.05 mm or less, or 0.04 mm or less. As shown in FIGS. 5A and 5B, the recess 510 includes a curved surface and, in such embodiments, can include a semi-circular or semi-oval shape. In some embodiments, the recess 510 can include non-curved surfaces and/or other shapes, such as a "box" shape in which the recess 510 includes sidewalls and a flat or non-curved base surface extending between the sidewalls, or a conical or pyramidal shape and/or "V" shape in which the recess 510 includes sidewalls that converge toward one another.

The distal section 530 can include a helical void or cut 434 extending along at least a portion of the length of the distal section 530, as previously described with reference to FIGS. 4A and 4B. As shown in FIGS. 5A and 5B, the cut 434 can include a proximalmost point 436 at an intermediate portion (e.g., spaced apart from a proximal end portion) of the distal section 530. That is, the cut 434 extends along only a portion of the length of the distal section 530. In such embodiments, the proximalmost point 436 may, for example, be spaced apart from the bumper section 500 (e.g., the distal end surface 502) by about 1.0 mm or less, 0.9 mm or less, 0.8 mm or less, 0.7 mm or less, 0.6 mm or less, or 0.5 mm or less. Positioning the proximalmost point 436 of the cut 434 at the intermediate portion of the distal section 530, as opposed to the proximal end portion, can prevent or limit bending at the proximal end portion of the distal section 530. Additionally or in lieu of the foregoing, positioning the proximalmost point 436 at the intermediate portion can decrease the likelihood that braid ends of a stent or mesh component disposed over the proximal restraint 119 become caught or tangled in the cut 434. For example, during delivery of a medical device through a patient's vasculature, the distal section 530 will bend along the cut 434, and the braid ends of the stent, which may be frayed, can become caught in the cut 434. By having the proximalmost point 436 of the cut 434 at the intermediate portion, the braid ends of the stent are spaced apart from the cut 434, and thus the likelihood of them becoming caught or tangled is decreased. In some embodiments the bumper section 400 can have an outer diameter of 0.030 inches or less, and the distal section 430 can have an outer diameter of 0.020 inches or less. In addition to or in lieu of the foregoing diameters, the bumper section 400 can project radially beyond the outer diameter of the distal section 430, e.g., by a distance of 0.007 to 0.015 inches. Such dimensions can be useful in some vascular applications such as neurovascular applications.

The proximal section 560 of the proximal restraint 119 can include a spacer or other tubular member that includes an outer profile 562 (e.g., outer surface, outer diameter, or outer cross-sectional dimension) extending longitudinally along a length of the proximal section 560. The proximal section 560 can be configured (e.g., sized) to slidably receive a tubular member, such as tube 106 (FIGS. 1-2B). That is, the tube 106 can be disposed over the proximal section 560 to abut the bumper section 500. In some embodiments, the proximal section 560 can be configured to substantially fill the lumen of the tube 106, such that the tube 106 is secured to the proximal restraint 119, e.g., via friction between the outer profile 562 and inner surface of the tube 106. As shown in FIGS. 5A and 5B, the outer profile 562 includes a distal first region having a constant-diameter profile and a proximal second region having a tapered profile.

In some embodiments, the proximal section 560 can include an undercut section 509 (FIG. 5A) (e.g., a second undercut section) having a recess 512 relative to an abutting surface (e.g., the outer profile 562). The recess 512 can include the features (e.g., shape, dimension, etc.) described with reference to the recess 510. For example, the recess 512 can include a depth ($D_3$) and a width ($W_3$) similar or identical to the respective depths (e.g., depth ($D_2$)) and widths (e.g., width ($W_2$)) previously described. The dimensions of the recesses 510, 512 may be the same or differ from one another.

As shown in FIG. 5B, the recess 512 is formed in the outer profile 562 at a distal end portion of the proximal section 560 and abuts or is contiguous to the proximal end surface 504 of the bumper section 500. In some embodiments, the outer profile 562 can have similar or identical dimensions as the outer profile 532 of the distal section 530, and can thus define the longitudinal cylindrical surface (CS). The recess 512 can be disposed circumferentially in the outer profile 562 such that the recess 512 extends inward of the longitudinal cylindrical surface (CS) toward the central longitudinal axis (C). Stated differently, the recess 512 is disposed circumferentially around the lumen 440 of the proximal restraint 119 such that the recess 512 has (a) a continuous surface circumferentially surrounding the lumen 440 and (b) an inwardmost point inward of the longitudinal cylindrical surface (CS). In some embodiments, the second recess 512 can enable a distal portion of a tubular member (e.g., the distal portion 118 of the tube 106 (FIGS. 2A and 2B)) disposed over the proximal section 560 to engage the proximal end surface 504 of the bumper section 500. In such embodiments, the distal portion of the tubular member can be positioned flush or substantially flush with the proximal end surface 504 such that no substantial gap exists therebetween. A flush or substantially flush interface between the distal portion of the tubular member and proximal end surface 504 can create a relatively more secure connection between the tubular member and the proximal restraint 119.

Aspects of the present technology, including embodiments of the proximal restraint shown in FIGS. 4A-5B, may be altered and/or combined to form additional embodiments. For example, FIG. 6 is a side, cross-sectional view of another embodiment of the proximal restraint 119 that combines certain features of FIGS. 4A and 4B with those of FIGS. 5A and 5B. As shown in FIG. 6, the proximal restraint 119 includes the proximal section 460 and bumper section 400 described with reference to FIGS. 4A and 4B, and the distal section 530 described with reference to FIGS. 5A and 5B. As previously described, the bumper section 400 includes the recess 410 formed circumferentially in the distal end surface 412 and extending proximal of the plane (Pi). The distal section 530 includes the recess 510 formed circumferentially in the outer profile 532 and extending inward of the longitudinal cylindrical surface (CS). As shown in FIG. 6, the recesses 410, 510 abut or are contiguous with one another. Including the recesses 410, 510, as opposed to just one of the recesses 410, 510, can increase the likelihood that the stent or other interventional element disposed over the proximal restraint 119 will be received by the recess 410 e.g., to inhibit or prevent the stent or other interventional element from traveling proximally beyond the proximal restraint 119.

CONCLUSION

This disclosure is not intended to be exhaustive or to limit the present technology to the precise forms disclosed herein. Although specific embodiments are disclosed herein for illustrative purposes, various equivalent modifications are possible without deviating from the present technology, as those of ordinary skill in the relevant art will recognize. In some cases, well-known structures and functions have not been shown and/or described in detail to avoid unnecessarily obscuring the description of the embodiments of the present technology. Although steps of methods may be presented herein in a particular order, in alternative embodiments the steps may have another suitable order. Similarly, certain aspects of the present technology disclosed in the context of particular embodiments can be combined or eliminated in other embodiments. Furthermore, while advantages associated with certain embodiments may have been disclosed in the context of those embodiments, other embodiments can also exhibit such advantages, and not all embodiments need necessarily exhibit such advantages or other advantages disclosed herein to fall within the scope of the present technology. Accordingly, this disclosure and associated technology can encompass other embodiments not expressly shown and/or described herein.

Throughout this disclosure, the singular terms "a," "an," and "the" include plural referents unless the context clearly indicates otherwise. Similarly, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. The terms "about" or "substantially" are used throughout this disclosure, and when preceding a numerical value or dimension mean plus or minus 10% thereof. Additionally, the terms "comprising" and the like are used throughout this disclosure to mean including at least the recited feature(s) such that any greater number of the same feature(s) and/or one or more additional types of features are not precluded. Directional terms, such as "upper," "lower," "front," "back," "vertical," and "horizontal," may be used herein to express and clarify the relationship between various elements. It should be understood that such terms do not denote absolute orientation. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics may be combined in any suitable manner in one or more embodiments.

The invention claimed is:

1. An interventional element delivery system, comprising:
 a core assembly sized for insertion into a corporeal lumen, the core assembly comprising—
   an elongate member having a distal segment; and
   a proximal restraint coupled to or extending over the distal segment of the elongate member, the proximal restraint including—
     a bumper section;
     an elongate distal section distal to the bumper section;
     a lumen extending through the bumper and distal sections; and
     an undercut section at least partially surrounding the lumen;
 an interventional element having a proximal end portion and a distal end portion opposite the proximal end portion along a longitudinal dimension of the interventional element, the interventional element extending along the distal segment of the elongate member such that the undercut section of the proximal restraint receives the proximal end portion of the interventional element and limits proximal translation of the proximal end portion of the interventional element and the distal end portion of the interventional element is positioned distal to the proximal restraint; and
 a tubular member configured to be positioned over the core assembly and the interventional element such that, when the interventional element is positioned within the tubular member, the interventional element assumes a compressed configuration, and wherein the tubular member is configured to be proximally retracted relative to the interventional element and the core assembly such that the interventional element radially expands from its distal end portion to its proximal end portion.

2. The system of claim 1, wherein the undercut section comprises a recess formed in the bumper section.

3. The system of claim 1, wherein the undercut section is radially peripheral to the distal section.

4. The system of claim 1, wherein the bumper section comprises a distal end portion including a surface defining a plane, and wherein a portion of the undercut section is proximal to the plane.

5. The system of claim 4, wherein a proximalmost point of the undercut section is separated from the plane by at least about 0.05 millimeters.

6. The system of claim 4, wherein a proximalmost point of the undercut section is separated from the plane by no more than 0.1 millimeters.

7. The system of claim 1, wherein the bumper section includes a first radial outer surface and the distal section includes a second radial outer surface, and wherein the undercut section is positioned between the first radial outer surface and the second radial outer surface.

8. The system of claim 1, wherein the undercut section comprises a recess formed in the distal section.

9. The system of claim 8, wherein the undercut section abuts the bumper section.

10. The system of claim 8, wherein the distal section includes an outer surface defining a cylindrical surface extending longitudinally around the lumen, wherein an innermost portion of the undercut section is inward of the cylindrical surface.

11. The system of claim 10, wherein the innermost portion of the undercut section is separated from the cylindrical surface by at least about 0.05 millimeters.

12. The system of claim 1, wherein the interventional element comprises a mesh or plurality of braided filaments.

13. The system of claim 1, wherein the distal segment of the elongate member extends through the lumen.

14. The system of claim 1, wherein the core assembly is configured to engage the interventional element such that the interventional element can be resheathed into the tubular member after the interventional element has partially radially expanded.

15. The system of claim 14, wherein the core assembly comprises an engagement member positioned distal of the proximal restraint, the engagement member having one or more projections configured to engage the interventional element.

* * * * *